United States Patent
Moser

(10) Patent No.: US 10,398,534 B2
(45) Date of Patent: Sep. 3, 2019

(54) ONE-PART TOOTH IMPLANT, DEVICE FOR BENDING AN IMPLANT, AND METHOD FOR BENDING AN IMPLANT

(71) Applicant: Hager & Meisinger GmbH, Neuss (DE)

(72) Inventor: Walter Moser, Erlinsbach (CH)

(73) Assignee: HAGER & MEISINGER GMBH, Neuss (DE)

(*) Notice: Subject to any disclaimer, the term of this patent is extended or adjusted under 35 U.S.C. 154(b) by 0 days.

(21) Appl. No.: 14/897,873

(22) PCT Filed: Jun. 13, 2013

(86) PCT No.: PCT/EP2013/001759
§ 371 (c)(1),
(2) Date: Dec. 11, 2015

(87) PCT Pub. No.: WO2014/198282
PCT Pub. Date: Dec. 18, 2014

(65) Prior Publication Data
US 2016/0143712 A1      May 26, 2016

(51) Int. Cl.
*A61C 8/00*      (2006.01)

(52) U.S. Cl.
CPC .......... *A61C 8/0075* (2013.01); *A61C 8/0012* (2013.01); *A61C 8/0025* (2013.01);
(Continued)

(58) Field of Classification Search
CPC ... A61C 8/0089; A61C 8/0053; A61C 8/0093; A61C 2008/0046; A61C 2204/00;
(Continued)

(56) References Cited

U.S. PATENT DOCUMENTS

| | | | |
|---|---|---|---|
| 1,141,916 A * | 6/1915 | Anderer | A61C 7/04 248/101 |
| 3,377,705 A | 4/1968 | Tofflemire | |

(Continued)

FOREIGN PATENT DOCUMENTS

| | | |
|---|---|---|
| CH | 44706 | 9/1909 |
| CH | 01632-10 | 1/2012 |

(Continued)

OTHER PUBLICATIONS

3M ESPE MDI Mini-Dental-Implantate, Technisches Produktprofil, 3M ESPE Technical Product Profile, Oct. 2012.
(Continued)

*Primary Examiner* — Nicholas D Lucchesi
(74) *Attorney, Agent, or Firm* — Neal, Gerber & Eisenberg LLP; Kevin A. O'Connor

(57) ABSTRACT

The invention relates to an implant (10) for anchoring in the human or animal maxilla or mandible, a device (100) (an instrument) for bending an implant, a system, which includes an implant (10) and a device (100) for bending an implant, and a method for bending an implant. As a result of the bending geometry, an implant (10) is provided which is bendable in a simple and materially-careful manner, in particular after implantation, i.e., already anchored in the jaw bone. The device (100) for bending the implant (10) enables, due to the pliers-shaped design having corresponding holding (113) and support (123) units, the bending of the implant in a simple manner, in particular the bending after implantation thereof, so that a treatment which protects the implantation region is ensured, in particular, no damage of the bone bed is induced. In addition, a method for bending the implant (10) is provided.

19 Claims, 9 Drawing Sheets

(52) U.S. Cl.
CPC .......... *A61C 8/0089* (2013.01); *A61C 8/0053* (2013.01); *A61C 2008/0046* (2013.01)

(58) Field of Classification Search
CPC .......... A61C 19/00; B21D 7/02; B21D 7/024; B21D 7/063; B25B 3/00; B25B 7/00; B25B 9/00; B25B 13/00; B25B 27/146; B23P 19/04; B23P 11/00; B23P 11/005; H01R 43/042
USPC ................. 433/159, 160; 72/457, 458, 409.1
See application file for complete search history.

(56) References Cited

U.S. PATENT DOCUMENTS

| | | | | |
|---|---|---|---|---|
| 3,745,665 | A * | 7/1973 | Shilliday | A61C 19/04 33/514 |
| 4,276,026 | A * | 6/1981 | Edelman | A61C 8/005 433/141 |
| 4,277,237 | A | 7/1981 | Dermer | |
| 4,645,453 | A | 4/1987 | Niznick | |
| 5,074,790 | A | 12/1991 | Bauer | |
| 5,107,559 | A * | 4/1992 | O'Reilley | A01L 11/00 7/127 |
| 5,120,221 | A | 6/1992 | Orenstein et al. | |
| 5,312,255 | A | 5/1994 | Bauer | |
| 5,511,297 | A * | 4/1996 | Cross | B25B 7/02 29/243.56 |
| 5,661,886 | A * | 9/1997 | Smith | B25B 7/02 29/243.5 |
| 6,050,123 | A * | 4/2000 | Fies | B25B 7/02 413/22 |
| 6,655,962 | B1 | 12/2003 | Kennard | |
| 9,527,195 | B1 * | 12/2016 | Deane | B25B 27/10 |
| 2006/0150699 | A1 * | 7/2006 | Garner | A61B 17/8863 72/31.04 |
| 2006/0216673 | A1 | 9/2006 | Park | |
| 2006/0257817 | A1 | 11/2006 | Shelton | |
| 2006/0264973 | A1 * | 11/2006 | Abdelgany | A61B 17/8863 606/109 |
| 2008/0254410 | A1 * | 10/2008 | Golden | A61C 3/14 433/159 |
| 2014/0342313 | A1 * | 11/2014 | De Basso | A61C 8/0042 433/159 |

FOREIGN PATENT DOCUMENTS

| | | | |
|---|---|---|---|
| CN | 2675077 | 2/2005 | |
| DE | 2522941 | 11/1976 | |
| DE | 2715178 | 10/1977 | |
| DE | 3241963 | 4/1984 | |
| DE | 3726616 | 9/1988 | |
| DE | 3742158 | 6/1989 | |
| DE | 3918309 | 12/1990 | |
| DE | 19633570 | 1/1998 | |
| DE | 29817955 | 1/1999 | |
| DE | 202007018726 | 3/2009 | |
| DE | 102008008763 | 8/2009 | |
| DE | 202008004960 U1 | 8/2009 | |
| DE | 202013002300 U1 | 7/2013 | |
| EA | 001319 | 2/2001 | |
| EP | 0657144 | 6/1995 | |
| EP | 0707835 | 4/1996 | |
| EP | 2438885 | 4/2012 | |
| EP | 2438885 A1 * | 4/2012 | .......... A61C 8/0051 |
| FR | 1423198 | 1/1966 | |
| GB | 1423198 | 1/1976 | |
| GB | 2450617 | 12/2008 | |
| WO | WO2000002495 | 1/2000 | |
| WO | WO2001012096 A1 | 2/2001 | |
| WO | WO2005020839 | 3/2005 | |
| WO | WO2005020839 A1 | 3/2005 | |
| WO | WO2007017257 A2 | 2/2007 | |
| WO | WO2008128756 | 10/2008 | |
| WO | WO 2014/139668 A1 | 9/2014 | |

OTHER PUBLICATIONS

Zipprich, et al., "Erfassung, Ursachen und Folgen von Mikrobewegungen am Implantat-Abutment-Interface," [Detection, causes, and consequences of micromovements at the implant-abutment interface], Implantologie 2007; 15(1), pp. 31-46.

Hartmann, "Vom Extensionsimplantat zur Hightech-Schraube," [From the extension implant to the high-tech screw], ZM 99, Issue 22A, Nov. 16, 2009.

International Search Report for PCT/EP2013/001759 dated Mar. 27, 2014, 10 pp.

* cited by examiner

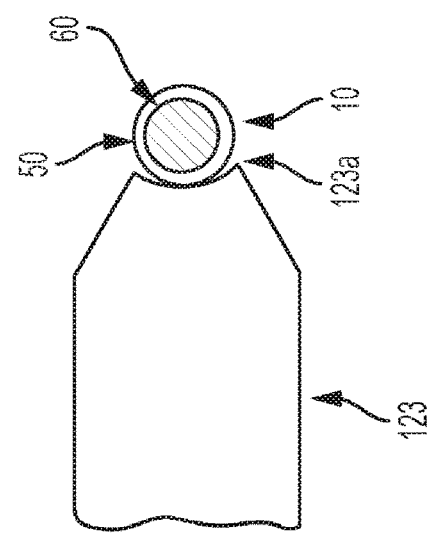
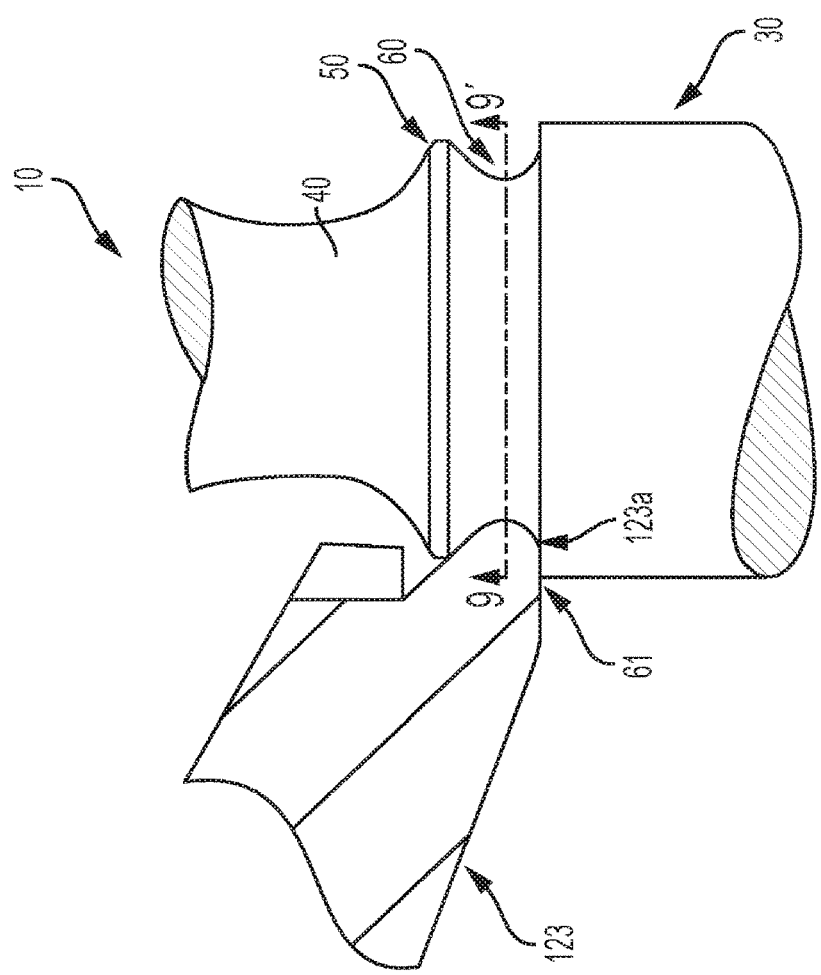
Fig. 9
Fig. 8

ONE-PART TOOTH IMPLANT, DEVICE FOR BENDING AN IMPLANT, AND METHOD FOR BENDING AN IMPLANT

CROSS-REFERENCE TO RELATED APPLICATION

This application is a national stage entry of International Patent Application No. PCT/EP2013/001759, filed on Jun. 13, 2013, the entire contents of which are incorporated herein by reference.

FIELD OF THE INVENTION

The invention relates to an implant for anchoring in the human (optionally also in the animal) maxilla or mandible, a device (an instrument) for bending an implant, a system which comprises an implant and a device for bending an implant, and a method for bending an implant.

BACKGROUND OF THE INVENTION

Tooth implants are either known as one-part constructions or as two-part constructions. In the two-part embodiment, firstly an artificial tooth root is implanted into the jaw bone and it is subsequently connected to a second component, the abutment stud. The connection to the abutment stud is either performed intraoperatively or after a healing phase of several weeks. If the connection point between artificial tooth root and abutment stud lies below the gum level, after the surgical covering with the mucosa, the tooth root can heal without stress. Therefore, secure healing, which is not disturbed by load-related micromovements, can be achieved in the bones. In cases in which a primary anchoring stability of the tooth root in the jaw bone permits healing which is free of micromovements under moderate load, an intraoperative mounting of the abutment stud can be performed. More rapid osseointegration of the tooth root can thus be achieved with sufficient primary stability because of the stimulation of the bone growth due to the mechanical stimuli.

The artificial tooth root of the two-part embodiment has a connecting mechanism for this purpose, by means of which the abutment stud can be mechanically connected fixedly to the tooth root. Known embodiments are formfitting connections, for example, hexagonal or octagonal connections secured using screws, or, alternatively, cone connections. The abutment stud carries the later dental-prosthetic construction, which is mounted either fixedly or removably.

Screw-shaped geometries (WO 2008/128756 A2) or cylindrical geometries (EP 0 657 144 A1) are frequently used as implant forms for the artificial tooth root, wherein in most applications the screw-shaped anchor is preferred, because of the advantages in the primary stability and the simplicity of the handling.

Titanium alloys have become established as materials for the components of the two-part systems, which are provided in the region of the artificial tooth root with rough, porous surfaces, which promote the osseointegration, by means of various technologies. In addition to the macrostructure and microstructure, calcium phosphate coatings of greatly varying crystallography and morphology are known as layers which promote the bone apposition.

After completed implantation, an abutment stud which is sought out for size and orientation can be used in the two-part implants. The alignment of the artificial tooth root, which is oriented according to the conditions of the jaw bone, is therefore independent of the alignment of the prosthetic abutment, which is oriented according to the conditions of the artificial tooth. In addition, these abutment studs can be adapted to a small extent by means of grinding processing.

The constructions which are used for the connection between artificial tooth root and abutment stud have to transmit the substantial chewing forces which are introduced via the dental-prosthetic construction into the abutment stud. In this case, both axial forces and lateral forces and also tilting torques and rotation torques act on this connection. One embodiment is known, for example, from DE 196 33 570 C1. A plug connection is described here, which is secured against rotation using radially applied grooves. Such connections are often clamped using a central screw.

Further embodiments are non-self-inhibiting conical plug connections, which are secured by means of interlocking hexagonal or octagonal connections against rotation and which are also installed using a central screw. Such a connection is described, for example, in WO 2008/128756 A2. These formfitting connections, which are secured against twisting, do enable the simple transfer of the rotation position between a dental model and the situation in the mouth of the patient, but do not permit free selection of the rotation position of the abutment stud. Depending on the technical embodiment, six or eight possible positions are usually predefined. This is of particular significance in the case of the screw-shaped bony anchoring, since the rotation position of the implant results therein due to the implantation and is not freely selectable.

An embodiment which enables a free selection of the rotation position of the abutment stud in relation to the artificial tooth root is described in EP 0 707 835 A1. A self-inhibiting cone connection is shown, which is secured using a central screw.

All of these installation connections are particularly critical with regard to the compromise between the smallest possible structural size, i.e., the smallest possible implant diameter, and the operational reliability. In addition to the security against loosening or fatigue fracture of the connection due to the cyclic chewing stress, high demands are to be placed on the leak-tightness, i.e., freedom from gaps, of this connection.

For manufacturing reasons, with the exception of the cone connection, all formfitting connections are subject to at least extremely small gaps. This applies for the unloaded state, but is increased markedly in the event of chewing-functional load. Constructions which are subject to gaps are easily populated with bacteria and thus act as loci, from which inflammations originate. Gap formation thus promotes bacterial contamination and may be correlated with the resorption of the cervical bone bed (Zipprich, H. et al.: Erfassung, Ursachen and Folgen von Mikrobewegungen am Implantat-Abutment-Interface [Detection, causes, and consequences of micromovements at the implant-abutment interface]. In: Zeitschrift Implantologie [Implantology magazine] 2007; 15(1), pages 31-46, Quintessenz Verlag).

In comparison, one-part implant systems are substantially simpler in the geometric design thereof, since a technical connection, which has to transmit the chewing forces with a high level of reliability, can be omitted. One-phase systems are therefore substantially more cost-effective. The design freedom in the cervical region is also not restricted by the necessity of a connection which occupies structural volume. Smaller implant diameters can therefore also be implemented using one-phase implants, with equal endurance strength.

In the case of cylindrical artificial tooth root geometries or other artificial tooth root geometries which are not to be inserted by means of a screwing movement, one-part tooth implants can be preformed, in the case of suitable materials, by bending in the region of the abutment stud or abutment region before the implantation. An adaptation of the alignment of the part accommodating the artificial tooth to the requirements of the prosthetic abutment can thus be performed. In the case of the screw-shaped tooth roots, which are advantageous for the anchoring, this is not possible because of the rotation position, which is predefined by the implantation position and which results by way of the screwing in up to a solid seat. However, an adaptation of the orientation of the coronal part (abutment region) after implantation by bending, because of the high forces which act on the bone bed during the bending, is not possible or is only possible in cases having very good anchoring conditions, i.e., with long lengths of the artificial tooth root and with good bone conditions. Generally, the use of shorter implants is indicated because of the jaw atrophy (usually also with softer bone quality), wherein bending after implantation would damage the bony bed.

One example of one-part implants are the leaf-shaped implants according to Linkow, as are described, for example, in DE 25 22 941 A1 (see also Hartmann, H.-J.: Vom Extensionsimplantat zur Hightech-Schraube [From the extension implant to the high-tech screw]. In: zm 99, issue 22A, 16, Nov. 2009, Deutscher Ärzte-Verlag).

Further implants are disclosed in DE 39 18 309 A1 (so-called Bauer screw), DE 32 41 963 C1 (so-called Münch screw made of ceramic material), and DE 37 26 616 C1 (so-called Ledermann screw).

Known implants are often not adapted in the structure thereof to a bending process in the anchored state or are also not provided for this purpose.

In addition to the material titanium, the materials aluminum oxide ceramic and cobalt alloys have also been used for one-part tooth implants, wherein these materials from the group of ceramics and cobalt alloys have not proven themselves because of the lesser suitability for osseointegration. The prior art are presently surfaces based on titanium, which are microstructured by coatings or by targeted partially acting ablation. In particular blasting and etching methods are used as ablation methods, frequently in combination.

Only a few specific instruments are known for adapting dental constructions or dental components by targeted deformation in conjunction with dental implants. An instrument is known from DE 39 18 309 A1, which can engage on a coronal implant end. In this document (see also Bauer, E.: Die K. S. I. Bauerschraube [The KSI Bauer screw], 1987, KSI-Bauer-Schraube GmbH), a one-part implant having a bending zone between a coronal part and an anchoring part is described, wherein the adaptation of the implant is performed by bending after the implantation using the above-mentioned instrument. However, bending after implantation is only possible in the case of this arrangement with very long anchoring geometries and very good bone quality. The implementation of shorter anchoring geometries, as is necessary in the region of the mandible posterior teeth or in the case of low alveolar ridge height, is not possible, since a shorter implant causes excessively high reaction forces during the bending, which result in damage to the bony bed. Damage to the bony bed is also to be expected upon use in softer bones.

A bending instrument for a fixation pin is described in British patent application GB 2 450 617 A.

A further bending instrument is known from EP 2 438 885 A1.

Some instruments are very complex to produce and handle. If known arrangements are used, to carry out the intraoral adaptation by bending, extensive exposure of the alveolar ridge in the region of the implant is often necessary. Disadvantages for the patient can be linked thereto, for example, as a result of local bone loss due to the preceding surgical exposure. The soft tissue and bleeding of the operation wound make it more difficult to securely position the bending instrument at the point provided for it.

SUMMARY OF THE INVENTION

It is the object of the invention to provide a tooth implant, which is bendable in a simple and materially-careful manner, in particular also after implantation, i.e., already anchored in the jaw bone. It is a further object of the invention to provide a device for bending an object, in particular an implant, which enables the bending of the implant in a simple manner and in particular the bending after the implantation thereof such that a treatment which protects the implantation region is ensured, in particular that no damage of the bone bed is induced. In addition, the device is to be simply producible and simple and reliable in the handling. Furthermore, it is the object of the invention to provide a corresponding method for bending an object, in particular an implant, also after the implantation thereof.

The above-mentioned objects are achieved and the described advantages are achieved by the subjects of the appended independent claims, reproduced in the aspects described hereafter of the invention (also by the additionally described aspects). Preferred embodiments are contained in the dependent claims and in the following description, the examples, and the figures.

In a first aspect, the invention relates to a one-part tooth implant, wherein the implant comprises:
  an anchoring region,
  an abutment region,
  a bending region, which is arranged on an end of the abutment region facing toward the anchoring region, between the abutment region and the anchoring region,
  a bearing region, which is arranged on an end of the anchoring region facing toward the abutment region, between the bending region and the anchoring region,
wherein the bending region has a smallest cross section, which is arranged in a half of the bending region facing toward the anchoring region,
wherein the cross section of the bending region continuously enlarges, originating from the smallest cross section toward an end of the bending region facing toward the abutment region.

In a second aspect, the invention relates to a one-part implant for anchoring in the human (optionally also in the animal) maxilla or mandible, wherein the implant comprises:
  an anchoring region for introduction into the maxilla or mandible,
  an abutment region for receiving a dental-prosthesis construction,
  a bending region, which is arranged on an end of the abutment region facing toward the anchoring region, between the abutment region and the anchoring region,
  a bearing region for applying a device for bending the implant (bending device), wherein the bearing region is arranged on an end of the anchoring region facing toward the abutment region, between the bending region and the anchoring region, wherein the bending region has a smallest cross section, which is arranged in a half of the bending region facing toward the anchoring region, wherein the cross section of the bending region continuously enlarges, originating from the smallest cross section toward an end of the bending region facing toward the abutment region.

In a third aspect, the invention relates to a one-part tooth implant, wherein the implant comprises:

an anchoring region, an abutment region, a bending region, which is arranged on an end of the abutment region facing toward the anchoring region, between the abutment region and the anchoring region, a bearing region, which is arranged on an end of the anchoring region facing toward the abutment region, between the bending region and the anchoring region, wherein the bending region has a smallest cross section, which is arranged on an end of the bending region facing toward the anchoring region, wherein the cross section of the bending region continuously enlarges, originating from the smallest cross section toward an end of the bending region facing toward the abutment region.

In a fourth aspect, the invention relates to a one-part implant for anchoring in the human (optionally also in the animal) maxilla or mandible, wherein the implant comprises:

an anchoring region for introduction into the maxilla or mandible, an abutment region for receiving a dental-prosthesis construction, a bending region, which is arranged on an end of the abutment region facing toward the anchoring region, between the abutment region and the anchoring region, a bearing region for applying a device for bending the implant (bending device), wherein the bearing region is arranged on an end of the anchoring region facing toward the abutment region, between the bending region and the anchoring region, wherein the bending region has a smallest cross section, which is arranged on an end of the bending region facing toward the anchoring region, wherein the cross section of the bending region continuously enlarges, originating from the smallest cross section toward an end of the bending region facing toward the abutment region.

An essential point of the invention according to the first to fourth aspects is the special design of the bending geometry, i.e., the bending region. The smallest cross section is in a region of the bending region facing toward the anchoring region, as close as possible to the corresponding end of the bending region. Since the cross section of the bending region continuously widens originating from the smallest cross section toward the abutment region, the implant or the abutment region is movable (bending) in relation to the anchoring region by means of a suitable instrument into an orientation suitable for the supply with a dental-prosthesis abutment, wherein the deformation in the bending region is formed such that critical bending deformations (locally high concentrations) do not occur anywhere. The deformation thus extends over the length of the bending region (in an extension direction or longitudinal direction of the implant) such that it is non-critical, materially-harmless, and/or also materially-careful for the material. That is to say, because of the design of the bending region having the positioning of the smallest cross section close to the end of the bending region which faces toward the anchoring region, and the continuous enlargement of the cross section of the bending region, originating from the smallest cross section toward the end of the bending region facing toward the abutment region, the bending region is deformable in a materially-harmless manner in the event of a bending stress over its extension.

That is to say, between the thinnest or smallest cross section and the chucking on the abutment region (more precisely: up to the end of the bending region), the cross section of the bending region enlarges so that, under the effect of the bending torque, which increases linearly toward the abutment region (in the event of bending stress), after exceeding the yield stress, the flowing procedures are homogeneously distributed in this material volume and no local damage of the material microstructure thus results. The bending region is designed so that buckle-free bending is achievable upon application of a bending torque.

Due to the corresponding design of the geometry of the bending region, the deformation along the bending zone can also be concentrated in a region provided for it. This can be significant in conjunction with the later functional stress of the tooth implant.

Further embodiments of the invention according to the first to fourth aspects are specified hereafter. That is to say, all embodiments relate to all above-mentioned aspects of the invention, namely to the first aspect, the second aspect, the third aspect, and also to the fourth aspect.

Diverse terms are found in the literature for the individual sections, parts, or regions of an implant. The anchoring region can also be referred to as the enossal part/region, i.e., the part/region located in the bone, while the abutment region can also be referred to as the coronal part/region or also as the abutment, abutment part/region.

The regions of the implant extend in a longitudinal direction or extension direction of the implant, wherein the cross section (also the respective cross section) extends transversely to the longitudinal direction or extension direction.

The cross section of the bending region enlarges continuously or is formed continuously enlarging, originating from the smallest cross section.

The anchoring region is designed such that it can be introduced into a or the maxilla or mandible bone of a human (optionally also of an animal), the abutment region is designed for receiving a dental-prosthesis construction, the bending region is designed such that it is bendable, and/or the bearing region is designed such that a device for bending the implant can engage or be applied thereon or is applicable thereon, in particular, an element, which is provided for this purpose, of the device for bending the implant can engage or be applied thereon or is applicable thereon.

The continuous enlargement or widening is preferably provided as a uniform enlargement or widening, for example, as a conical enlargement (widening conically, originating from the smallest cross section). It can be designed as a linear, concave, or convex enlargement or widening.

In one embodiment, the bending region has a first radius-shaped geometry on the end facing toward the abutment region. This geometry is designed such that the cross section of the bending region furthermore continuously enlarges toward the end of the bending region facing toward the abutment region. That is to say, originating from the smallest cross section toward the end of the bending region facing toward the abutment region, the cross section of the bending region continuously enlarges throughout.

In one embodiment, the bending region has a second radius-shaped geometry on a or the end facing toward the anchoring region, which is designed such that the cross section of the bending region continuously enlarges, originating from the smallest cross section toward the end of the bending region facing toward the anchoring region.

In one embodiment, the smallest cross section on the second radius-shaped geometry is thus arranged at the end of the bending region facing toward the anchoring region.

The end zones of the bending region are each formed having radii to avoid notches. That is to say, originating from the end of the bending region facing toward the anchoring region, the geometry tapers in the coronal direction (in the direction of the abutment region) via a radius to the thinnest cross section, to then continuously widen in the direction of the abutment region. The transition from the end of the bending region facing toward the abutment region to the abutment region is again embodied by a radius.

In one embodiment, the abutment region is designed as an abutment cone, which tapers toward a free end of the abutment region and therefore of the implant, i.e., facing away from the anchoring region. Conical elements enable a precisely fitted, stable connection, of abutment region and prosthetic construction here, which can be designed as connected removably or fixedly to the abutment region.

The abutment region can have further geometry elements, for example, a central thread or grooves or planar surfaces applied along the cone.

The bearing region is designed in one embodiment as a groove-shaped region, i.e., for example, in the form of a channel, wherein the groove-shaped region is provided as an engagement region for the device for bending. That is to say, inter alia, on the bearing region, the device for bending is applicable, so that the object or the implant is mountable on or in the device. The bearing region is designed in one embodiment as a region depressed in relation to the surroundings. In other words: The bearing region is preferably designed as a groove-shaped region extending in a circumferential direction of the implant, or the bearing region preferably has an edge region extending in an extension direction of the implant, which is designed as curving inward (toward the implant).

In one embodiment, the bearing region has an edge region extending in an extension direction of the implant, which is designed as linear or curving outward (away from the implant, in a bead shape).

In one embodiment, a smallest cross section of the bearing region is designed to be larger than the smallest cross section of the bending region. This is preferably also the case if the bearing region is designed as a groove-shaped region.

For bending the implant, it is to be mounted on a further point provided for this purpose; the device for bending must thus be able to engage at a further point, for example, on the free end of the abutment region or on the abutment region here. The implant (or also another suitable object) may therefore be grasped in a suitable manner and brought into the desired shape. In one embodiment, the abutment region is designed so that is entirely or partially graspable. The implant can thus be mounted or grasped via the abutment region and the bearing region in the device for bending and can thus be bent.

In one embodiment, a collar-shaped element, which separates the bending region from the bearing region, is provided between the bending region and the bearing region. The collar-shaped element is thus arranged between the bending region and the bearing region. It can be designed as thickened and/or in a bead shape, for example.

If the bearing region is designed as a grooved (or groove-shaped) region, it preferably terminates with the collar-shaped element. In the case of other designs of the bearing region, as described above, an explicit collar-shaped element is preferably not provided, the bearing region is then simultaneously designed as the collar-shaped element.

A bending force can be introduced into the geometry of the bearing region by means of the device for bending. Between the bearing region and the torque-stable mount of the abutment region, the geometry of the bending region is designed so that in the event of bending stress, a controlled deformation takes place in the material volume of the bending region.

The bending region and the bearing region are used, because of the design thereof, at the same time for the accumulation of the oral mucosa and, due to the shaping thereof, form an additional resistance against the penetration of microbes (labyrinth, multiple platform switching). Due to the tapered geometry and the adjoining collar (collar-shaped element), a barrier results against the penetration of microbes from the oral cavity into the region of the bony anchoring in the form of a labyrinth. In addition, the collar-shaped element is used as a reinforcement. That is to say, in the region of the collar-shaped element of the implant, the achieved deformation is equal to zero because of the reinforcing effect and the proximity to the mounting on the bearing region. In addition, the collar-shaped region preferably also forms the bearing region.

The abutment region, the anchoring region, the bending region, the bearing region, and/or the collar-shaped element are preferably designed as rotationally symmetrical regions (or elements) (except for a thread structure of the anchoring region).

In one embodiment, the implant is formed from a plastically deformable titanium material. For example, pure titanium or titanium alloys are used for this purpose, for example, Ti6Al4V, Ti6Al7Nb. Alternatively, highly plastically deformable beta-titanium alloys or tantalum alloys can also be used. In particular the bending region is to be designed so that no previous damage of the material arises due to the bending. Brittle or crack-sensitive materials are therefore excluded from the concept of intraoperative adaptation by targeted, controlled bending.

Because of the linear elastic properties of the implant material, the implant must be over-bent by a specific amount, by which the implant material rebounds, to achieve the desired bending angle. This amount is oriented according to the material used and the geometry of the bending zone. This value can be ascertained and depicted for the user, for example, in a table or as a display on the bending instrument.

In one embodiment, the anchoring region has a first threaded portion and a second threaded portion, wherein the first threaded portion is arranged between the bearing region and the second threaded portion.

In one embodiment, the first threaded portion has a flank depth which is less than a flank depth of the second threaded portion. In one embodiment, the first threaded portion is designed as a double-start thread and the second threaded portion is designed as a single-start thread. The double-start thread having less flank depth is provided for the anchoring in the more solid cortical component in the jaw bone and the single-start thread having greater flank depth is provided for the anchoring in the spongy region of the jaw bone.

In one embodiment, the two threads of the threaded portions have the same pitch, so that no conflicts arise during the insertion of the screw profile. The first threaded portion and/or the second threaded portion preferably each have a cutting edge, which are arranged on the respective ends of the threaded portions facing away from the abutment region (apical ends). The function of a self-tapping thread is thus provided.

During the implantation, the bony bed is firstly preprepared by means of a drilling procedure. A suitable instrument, for example, a thread cutter or thread shaper, is used to prepare the anchoring of a thread geometry of the artificial tooth root in the bone, or a self-tapping thread is used in the artificial tooth root, as already described above. The actual implantation is then performed by means of a screwing-in instrument, which securely grasps the implant and enables the application of the screwing-in torque using a hand wheel, a ratchet, or a motorized drive.

Depending on the bone quality, the thread has to be cut (very hard), or it is preformed by a type of displacement (moderate), or the thread creation can be omitted (relatively soft).

The cutting edges on the thread flanks and possible chip flutes are designed so that the implant itself forms a thread structure in a preformed, still smooth cavity with increasing screwing-in depth. The bone thread thus resulting results by cutting or by displacement, whereby the screwing-in characteristic and the clamping properties, i.e., the primary stability, are determined.

In addition to the thread-shaped macrostructure, the region of the artificial tooth root is preferably provided with a roughened microstructure in particular, produced by application or targeted ablation. These rough structures are used, on the one hand, for exciting the bone accretion, on the other hand, for the permanent fixed interlocking with the accreted bone structures after the healing phase. Such microstructures are created, for example, by blasting methods, by etching methods, or by a combination of these two ablation methods, or by an application method, for example, coating with a titanium plasma spray layer.

The implantation is preferably performed so that the end of the first threaded portion facing in the direction of the abutment region is located at or slightly below the bone level. Because of the anatomical conditions, i.e., the curvature of the alveolar ridge, the bearing region then lies either above the bone level or partially also at or slightly below the bone level.

The bearing region (for example, groove-shaped region) for receiving or applying the device for bending preferably directly adjoins the threaded region (anchoring thread) of the anchoring region.

During the bending of the implant, the bending torque Mb increases linearly originating from the force engagement location in the bearing region toward the fixed chucking at the abutment region. In the region of the collar-shaped element (explicitly provided or in the form of the bearing region) of the implant, the targeted deformation is equal to zero, as already mentioned above, because of the reinforcing effect and the proximity to the force introduction. In the cross section adjoining in the direction of the abutment region, which tapers, in particular tapers in a radius shape, the bending stress increases up to the smallest cross section. Between the smallest cross section and the end of the bending region facing toward the abutment region, the cross section of the geometry of the bending zone enlarges, as also mentioned above, so that under the effect of the bending torque, which increases linearly in the direction of the abutment region, after exceeding the yield stress, the flow procedures are distributed homogeneously in this material volume and thus no local damage of the material microstructure results.

In a fifth aspect, the invention relates to a bending device, which comprises the following:
- a first leg and a second leg, which are articulately jointed with one another and are actuatable corresponding to a scissors or pliers tool,
- a holding unit, wherein the holding unit is arranged on a distal end of the first leg,
- a support unit, wherein the support unit is arranged on a distal end of the second leg, wherein the holding unit and the support unit are movable in relation to one another by means of the first leg and the second leg.

In a sixth aspect, the invention relates to a device for bending an implant, preferably a one-part implant. The implant is anchored in the human (optionally also in the animal) maxilla or mandible or is also provided for anchoring in the human (optionally also in the animal) maxilla or mandible. The device has the following:
- a first leg and a second leg, which are articulately jointed with one another and are actuatable corresponding to a scissors or pliers tool,
- a holding unit for the bending-torque-stable fixing of an abutment region of the implant or of at least a part of the abutment region of the implant,
- wherein the holding unit is arranged on a distal end of the first leg,
- a support unit for introducing a force into a bearing region of the implant,
- wherein the support unit is arranged on a distal end of the second leg, wherein the holding unit and the support unit are movable in relation to one another by means of the first leg and the second leg.

In a seventh aspect, the invention relates to a device for bending an implant, preferably a one-part implant. The implant is anchored in the human (optionally also in the animal) maxilla or mandible or is also provided for anchoring in the human (optionally also in the animal) maxilla or mandible. The device has the following:
- a first leg and a second leg, which are articulately jointed with one another and are actuatable corresponding to a scissors or pliers tool,
- a holding unit for the bending-torque-stable fixing of an abutment region of the implant or of at least a part of the abutment region of the implant,
- wherein the holding unit is arranged on a distal end of the first leg,
- a support unit for introducing a force into a bearing region of the implant,
- wherein the support unit is arranged on a distal end of the second leg, wherein the holding unit and the support unit are movable in an arc shape in relation to one another by means of the first leg and the second leg.

In an eighth aspect, the invention relates to a device for bending an implant, preferably a one-part implant. The implant is anchored in the human (optionally also in the animal) maxilla or mandible or is also provided for anchoring in the human (optionally also in the animal) maxilla or mandible. The device has the following:
- a first leg and a second leg, which are articulately jointed with one another and are actuatable corresponding to a scissors or pliers tool, a holding unit for fixing of an abutment region of the implant or of at least a part of the abutment region of the implant,
wherein the holding unit is arranged on a distal end of the first leg,
a support unit for application to a bearing region of the implant,
wherein the support unit is arranged on a distal end of the second leg,
wherein the holding unit and the support unit are movable in relation to one another by means of the first leg and the second leg.

In a ninth aspect, the invention relates to a device for bending an implant, preferably a one-part implant. The implant is anchored in the human (optionally also in the animal) maxilla or mandible or is also provided for anchoring in the human (optionally also in the animal) maxilla or mandible. The device has the following:
 a first leg and a second leg, which are articulately jointed with one another and are actuatable corresponding to a scissors or pliers tool,
 a holding unit for fixing of an abutment region of the implant or of at least a part of the abutment region of the implant,
 wherein the holding unit is arranged on a distal end of the first leg,
 a support unit for application to a bearing region of the implant,
 wherein the support unit is arranged on a distal end of the second leg,
wherein the holding unit and the support unit are movable in an arc shape in relation to one another by means of the first leg and the second leg.

In a tenth aspect, the invention relates to a device for bending an object (device or instrument for bending an object). The device for bending an object comprises:
 a first leg and a second leg, which are articulately jointed with one another and are actuatable corresponding to a scissors or pliers tool,
 a holding unit for the bending-torque-stable fixing of a mounting region of the object or of at least a part of the mounting region of the object,
 wherein the holding unit is arranged on a distal end of the first leg,
 a support unit for introducing a force into a bearing region of the object,
 wherein the support unit is arranged on a distal end of the second leg,
wherein the holding unit and the support unit are movable in relation to one another, preferably in an arc shape in relation to one another, by means of the first leg and the second leg. The legs are thus movable in relation to one another such that the object is bendable on a region provided for this purpose.

An essential point of the invention according to the fifth to tenth aspects is that, using the device or the devices, a bending procedure can be performed in a simple manner on an implant provided for this purpose in particular, which is already placed in the jaw bone. In this case, a bending stress is generated in the bending region of the implant such that locally high concentrations are avoidable and the material is thus not damaged. This is possible by way of the above-described special design of the bending region of the implant. After completed implantation of the implant in the bone, the abutment region of the implant can be bent in a targeted manner at a defined angle (bending angle) in relation to the root-side anchoring region by means of the device/the devices by way of a closing movement of the legs, without the root-side anchoring region being loaded by bending forces. Since the device for bending (bending instrument) neutralizes the forces and torques between bearing region and abutment region, the enossal region and therefore the bone enclosing the anchoring region do not experience forces or torques from the bending process.

The implant is thus bendable via the bending region during a closing movement of the legs. In other words: As a result of the relative movement of the legs toward one another, the implant is bendable in a region provided for this purpose during a closing movement of the legs.

The support unit is therefore designed and/or arranged such that the support unit is applicable to the bearing region of the implant during a closing movement of the legs and/or the force can be introduced into the bearing region of the implant during a closing movement of the legs.

The bending is also achieved by the closing movement of the legs for the invention according to the tenth aspect.

The alignment of the coronal component, in particular the abutment region of the implant, may therefore be adapted to the individual conditions of the implantation region and the patient by monitored bending by means of the devices. The devices are thus also used for the geometric adaptation of the implant after completed implantation.

In addition, using the described device or the described devices, only a very partial surgical exposure of the implant in the region of the alveolar ridge is necessary. The surroundings on the alveolar ridge only have to be partially exposed, i.e., in the region of the engagement of the support unit. In addition, the handling of the device(s) during the operation is very simple, since complete visual monitoring in the bleeding operation field is not necessary for secure use (the surroundings on the alveolar ridge do not have to be completely visible). Since the support unit is movable in relation to the holding unit, corresponding to a scissors or pliers tool, the support unit approaches the alveolar ridge, in particular in an arc shape, such that the distance to the alveolar ridge gradually decreases. That is to say, as long as the support unit is not in the immediate vicinity of the implant (for example, when receiving the implant in the device for bending), the alveolar ridge surrounding the implant is not impaired by the support unit. Using the device or the devices, a careful adaptation of the anchored implant can thus be performed both with respect to the implant and also to the implantation region.

Further embodiments of the invention according to the fifth to tenth aspects are specified hereafter. That is to say, all embodiments relate to all above-mentioned aspects of the invention, namely to the fifth aspect, to the sixth aspect, to the seventh aspect, to the eighth aspect, to the ninth aspect, and to the tenth aspect.

The following explanations and statements generally relate to the implant, in particular to an implant already anchored in the jaw bone. If expedient, the explanations also relate to another object to be bent (for example, another type of metal pin), even if this is not explicitly mentioned. The object has to have a mounting region for this purpose, using which it is fixable in the holding unit. In addition, a bearing region has to be provided, at which a force can be introduced. The object is then bendable by means of the bending device at a location provided for this purpose.

The implant may also be bent in a desired direction using the device if it is not anchored in the jaw bone. The implant is then to be positioned in the device and is held via the holding unit and the support unit. The bending procedure can then be performed by the movement of the legs in relation to one another. This can be expedient in particular for another object, which is not anchored at one end. However, objects which are anchored, i.e., fastened at one end, may also thus be bent by means of the device.

"Bending-torque-stable" is to be understood, for example, as a mechanical fixation of the implant, which is capable of absorbing a single-axis or multiaxis bending torque.

As already described above, it is true for the device, as a result of the relative movement of the legs toward one another, that during a closing movement of the legs, the implant is bendable at a region provided for this purpose. The implant is preferably accommodated in the device with the legs open and is then positioned and bent by the closing movement.

The holding unit is designed such that an abutment region of the implant or at least a part of the abutment region is fixable, preferably fixable in a bending-torque-stable manner. The support unit is designed such that a force can be introduced into a bearing region of the implant during a closing movement of the legs, and/or it is applicable to a bearing region of the implant during a closing movement of the legs.

For all embodiments, it is preferably true that the elements of the device for bending are designed such that they engage correspondingly on the implant (or on another suitable object) in use of the device or also in use of the individual elements, so that the desired bending operation is executable.

The distal ends are in this context the ends of the legs (distal end of the device), which face toward the patient and therefore face away from an operator, for example, the dentist, and on which the actual functional elements of the device are provided. Proximal ends of the legs (at the proximal end of the device) are provided for the handling by the operator and can be designed accordingly. For example, explicit handles or handle elements can be provided on the proximal ends, which are adapted to the fingers of the operator and thus ensure better handling. Scissors-like handle elements could also be provided, so that the device for bending is actuatable similarly to a cutting instrument (scissors).

The legs can also be referred to as branches, instrument legs, or pliers legs.

In one embodiment, the holding unit and the support unit are movable in an arc shape in relation to one another by means of the first leg and the second leg. This enables the desired bending. That is to say, due to the movement of the legs in relation to one another, both the holding unit and also the support unit move in an arc shape (bending line of the bending region).

The holding unit is designed in one embodiment such that a bending-torque-stable mounting or fixing of the abutment region (or of at least a part of the abutment region) of the implant is possible in use. This mounting must be designed so that at least bending torques and transverse forces (transverse to an extension direction of the implant, longitudinal axis) can be absorbed. Rotation torques about the longitudinal axis of the implant (i.e., in the extension direction of the implant) and axial forces can, but do not necessarily have to be, absorbed by this holding unit. The holding unit can thus be designed, for example, such that a ring gap is provided between the abutment region and the holding unit, to avoid jamming. The holding unit can also extend beyond the abutment region in the direction of the anchoring region, but only enough that a bending procedure is ensured.

In one embodiment, the holding unit has a sleeve, which is arranged such that an implant anchored in the maxilla or mandible is receivable in the sleeve via an opening of the sleeve, which faces toward the implant in use. The sleeve structure enables bending-torque-stable receiving of the abutment region (optionally also only the receiving of at least a part of the abutment region), so that when force is introduced through the support unit on the bearing region, a secure hold is ensured (with respect to bending torques, not with respect to rotation torques). Alternatively, the abutment region or at least a part of the abutment region can also be chucked or clamped in a friction-locked manner, so that a torque can be introduced therein.

Independently of whether the implant is anchored, it can be received in the holding unit. This is also true for another object, which is freely accessible or is anchored at one end.

The sleeve is preferably arranged in a replaceable manner on the distal end of the first leg, so that various implants having various shapes and sizes of the abutment region are bendable. Different embodiments of the abutment region or different structural heights of the bending region can be necessary because of different thicknesses of the oral mucosa.

The abutment region of the implant is, for example, as already mentioned above, designed as a conical element and is suitable to be received in the holding unit, for example, in the sleeve here. In the case of the conical design of the abutment region, the sleeve can be designed so that, for example, a circular ring gap is provided between the received abutment region of the implant and the sleeve, to avoid jamming of the implant in the sleeve. Ring gaps can be provided in the range of 0.01 mm to 0.5 mm as suitable dimensions, a gap of 0.05 mm is preferably provided.

The support unit is designed in one embodiment such that via it a force introduction into the implant is performed, and it optionally positions the implant in the device. In use, the support unit contacts the implant in the bearing region and introduces the bending force therein by way of the relative movement of the legs. In the case of a ring gap in the holding unit or sleeve, the support unit additionally positions the implant in the axial direction. The device is simple to handle, in addition, complete visual monitoring in the bleeding operation field is not necessary for secure use of the device, since the design of the support unit does not require it.

In one embodiment, the support unit is designed as a one-part element. In a further embodiment, the support unit is designed as a hooked element.

In one embodiment, the support unit is designed and/or arranged such that the force, in use of the support unit or also in use of the device, i.e., with the implant introduced into the device, can be introduced into the bearing region on one side, preferably exclusively on one side, and/or in the bending direction, in which the implant is bent, preferably exclusively in the bending direction. That is to say, as soon as the implant is inserted into the device for bending, the support unit can be applied accordingly, so that the bending procedure can be carried out.

In one embodiment, the support unit is designed and/or arranged such that it can exclusively be applied to a single portion of the bearing region of the implant, preferably at one point or locally. That is to say, the hook or the hooked element engages in use on the implant in or at the bearing region (for example, channel), and touches it.

In one embodiment, the support unit is designed and/or arranged such that using it a portion of the bearing region is graspable without jamming, preferably exclusively without jamming. As already described above, a force introduction is only required in the bending direction. The bending can thus be performed in the desired direction in a simple manner by the holding of the implant in the holding unit.

In one embodiment, the support unit is designed and/or arranged such that using it (in use) the bearing region is exclusively graspable on a portion which is arranged on the side to be elongated of the implant or object. When the implant is thus positioned in the device, the engagement of the support unit is performed such that exclusively the region to be elongated of the implant faces toward the support unit.

In one embodiment, the support unit is arranged such that it faces in the direction of the distal end of the device, in a further embodiment, the support unit is arranged such that it faces in the direction of the proximal end of the device. The embodiment in which the support unit faces in the direction of the distal end of the device enables bending of the implant in the direction of the oral cavity, while the embodiment in which the support unit faces in the direction of the proximal end of the device enables bending of the implant in the direction of the oral opening.

The monitored bending procedure is thus carried out by a closing movement of the pliers legs either in the direction of the oral opening or in the direction of the oral cavity, because it is necessary for the use of the bending device on the patient that implants can be bent both in the direction of the oral opening and also in the opposite direction, i.e., in the direction of the oral cavity.

Because the support unit is designed as a one-part element, for example, as a hooked element, that can grasp the implant without jamming, the careful treatment of the implantation surroundings is provided. As already noted above, it is sufficient to expose the surroundings on the alveolar ridge, i.e., for example, the surroundings of the collar-shaped region, only partially, i.e., in the region of the engagement of the support unit, which enables the careful treatment of the surrounding tissue. That is to say, the support unit is designed to be as small as possible in its dimensions, to influence the implantation region as little as possible, on the one hand, and to keep the design of the device for bending (bending device) as simple as possible, on the other hand.

In one embodiment, the device has a guide unit for articulately joining the legs with one another and for moving the legs in relation to one another, preferably in an arc shape in relation to one another. The guide unit thus forms a type of joint. That is to say, the guide unit has elements which interlock such that a relative movement, preferably an arc-shaped relative movement, is possible between the legs and therefore between the holding unit and the support unit.

In one embodiment, the guide unit has at least one guide path (it can be designed as a guide slot or guide groove), which is arranged on the distal end of the second leg, and at least one guide element, which is arranged on the distal end of the first leg, wherein the guide element can be guided in the guide path for articulately joining the legs with one another and for moving the legs in relation to one another, preferably in an arc shape in relation to one another.

In one embodiment, the guide unit has the following: a first plate element having at least one first guide path and a second plate element having at least one second guide path on the distal end of the second leg, which are spaced apart opposite to one another so that a cavity is formed between the first plate element and the second plate element. In addition, the guide unit has at least one guide element on the distal end of the first leg, which is arranged in the cavity such that the guide element engages both in the first guide path and also in the second guide path and can be guided in the guide paths. In one embodiment, the holding unit on the distal end of the first leg extends through the cavity. The guide element is thus preferably arranged together with the holding unit on the distal end of the first leg.

Instead of the plate structure, another structural form can also be provided, for example, also an open structural form. Thus, only one plate element can also be provided or, for example, a flying mount. It is preferably provided that the plate elements or also one plate element carry or carries the support unit, wherein the holding unit can be guided on the plate element or the plate elements.

Plate-shaped structures have significant advantages over other shapes with respect to the small size and dimensions. The arrangement and the type of the juxtaposition of the components, i.e., for example, the plate-shaped elements, the support unit, and the holding unit, enable the provision of a space-saving arrangement, wherein the precise interaction of the units is ensured.

The guide path thus forms an opening or a groove, in which the guide element is receivable. The movement of the holding unit and the support unit follows a path curve, the path curve of the guide path, corresponding to the profile of the bending line of the bending region of the implant. The path curve (and therefore the guide path) can be circular, but can also be another path curve, adapted to the bending line of the bending region, for example, ellipsoidal.

Therefore, for example, a slotted guide is provided, which is used as a joint between the legs and enables the legs to be moved in a defined manner in relation to one another, corresponding to pliers. The leg having the fixed chucking (holding unit) thus moves on a defined path in relation to the leg which carries the support unit. The pivot point of the guided movement is preferably in the vicinity of the torque-resistant chucking (close to the end of the bending region facing toward the abutment region) and is fixed, but can also be variable.

In one embodiment, the support unit is designed as an element connecting the first plate element and the second plate element.

In one embodiment, two guide elements are arranged on the distal end of the first leg such that the holding unit is arranged between the guide elements. The guide elements are preferably arranged symmetrically with respect to the holding unit.

In one embodiment, the guide element is or the guide elements are designed as pin-shaped elements. Secure engagement in the guide path or guide paths is therefore ensured. Other elements, for example, a curved feather key, can also be used.

In one embodiment, a scale or measurement scale or scaling is arranged along the first guide path, preferably on the first plate element, and/or along the second guide path, preferably on the second plate element. A marking is then preferably arranged on the distal end of the first leg such that a bending angle of the implant (or also of the object), i.e., an angle between the abutment region and the anchoring region, is displayable. Additional visual monitoring of the bending procedure is therefore provided.

In one embodiment, a pointer unit is arranged or can be arranged on the holding unit, such that an orientation of the implant, in particular of the abutment region of the implant, in relation to the row of teeth of a patient is displayable. That is to say, the bending procedure can also hereby be additionally visually monitored.

In one embodiment, the guide path or each of the guide paths has a widening region which is designed and arranged as an enlarged region on one end of the guide path or of each guide path such that the guide element facing toward the respective widening region, i.e., for example, the pin-shaped element, is receivable in the respective widening region upon maximum opening of the legs. Therefore, a certain amount of play is permitted at the corresponding end of the respective guide path, for example, the guide slot, to deflect the pin-shaped element in this region. The support unit can therefore be moved away from the opening of the holding unit far enough that the implant or the abutment region thereof is insertable without obstruction into the holding unit. After receiving the implant, the guide element slides back into the play-free guide due to the closing procedure of the legs.

In arrangements which only have one guide path or similar unit, it also preferably has a corresponding widening region.

The bending device is preferably to be produced from one (optionally also multiple) high-strength instrument steel or steels because of the high requirements for the strength.

In an eleventh aspect, the invention relates to a system, which comprises at least one of the above-described implants, and at least one of the devices for bending an implant, as described above. Each of the disclosed implants may be used both with the device for bending in the direction of the oral opening and also with the device for bending in the direction of the oral cavity. In addition, each implant is combinable with each of the described devices.

In a twelfth aspect, the invention relates to a method for bending an implant, preferably a one-part implant. The implant is anchored in the human (optionally also in the animal) maxilla or mandible or is also provided for anchoring in the human (optionally also in the animal) maxilla or mandible. The method has the following steps:
  providing a device for bending an implant,
    having a first leg and a second leg, which are articulately jointed with one another and are actuatable corresponding to a scissors or pliers tool,
    bending-torque-stable fixing of an abutment region of the implant or of at least a part of the abutment region of the implant by means of a holding unit of the device,
    wherein the holding unit is arranged on a distal end of the first leg,
    introducing a force into a bearing region of the implant by means of a support unit of the device,
    wherein the support unit is arranged on a distal end of the second leg,
    actuating the first leg and the second leg of the device, such that the holding unit and the support unit are moved in relation to one another, preferably in an arc shape in relation to one another.

In a thirteenth aspect, the invention relates to a method for bending an implant, preferably a one-part implant. The implant is anchored in the human (optionally also in the animal) maxilla or mandible or is also provided for anchoring in the human (optionally also in the animal) maxilla or mandible. The method has the following steps:
  providing a device for bending an implant,
    having a first leg and a second leg, which are articulately jointed with one another and are actuatable corresponding to a scissors or pliers tool,
    fixing of an abutment region of the implant or of at least a part of the abutment region of the implant by means of a holding unit of the device,
    wherein the holding unit is arranged on a distal end of the first leg,
    applying a support unit of the device to a bearing region of the implant,
    wherein the support unit is arranged on a distal end of the second leg,
    actuating the first leg and the second leg of the device, such that the holding unit and the support unit are moved in relation to one another, preferably in an arc shape in relation to one another.

The implant, which is anchored in the jaw bone of a patient, is thus positioned and bent during a closing movement of the legs. Bending may also fundamentally be carried out without anchoring of the implant. This is also true for another object suitable for this purpose.

In one embodiment, the method for bending an implant, in particular an anchored implant, can be carried out using the devices for bending as are described above. The method can be carried out using any of the devices according to the fifth to ninth aspects.

Further embodiments of the invention result from the dependent claims.

BRIEF DESCRIPTION OF THE DRAWINGS

Exemplary embodiments of the invention are explained in greater detail hereafter on the basis of figures. In the figures:

FIG. 8 shows a portion of the support unit, in section, in a side view, FIG. 9 shows a portion of the support unit and a cross-section of a portion of the implant taken along a line 9-9' of FIG. 8, in a view from below.

DESCRIPTION OF PREFERRED EMBODIMENTS

Figure 1:
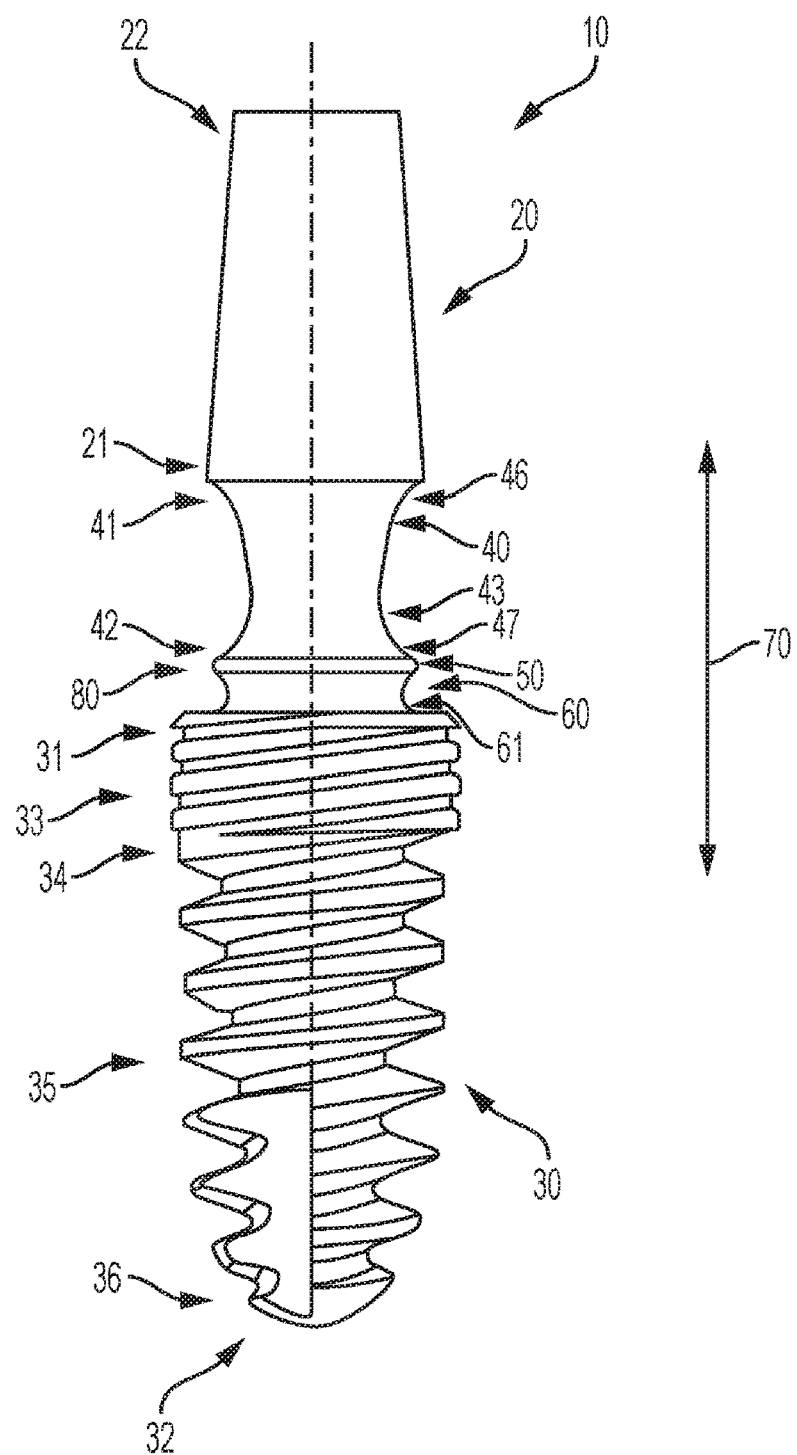
FIG. 1 shows an embodiment of an implant according to the invention.

In the following description, the same reference numerals are used for identical and identically acting parts.

FIG. 1 shows an embodiment of an implant 10 according to the invention having an abutment region 20, also referred to as an abutment, which is designed such that a dental-prosthesis construction (not shown) is fastenable thereon. In addition, the geometry of an artificial tooth root or an anchoring region 30 is shown. An end 31 of the anchoring region 30 facing toward the abutment region will be located, for example, at or (slightly) below a bone level 80 after the implantation. Furthermore a bending region 40, also referred to as a bending zone, is provided, a collar-shaped element 50, and a bearing region 60.

The abutment region 20 has an end 21 facing toward the anchoring region and a free end or coronal end 22. The anchoring region 30 has the end 31 facing toward the abutment region and a free end or enossal end 32.

The bending region 40 is arranged between the abutment region 20 and the anchoring region 30, more precisely between the abutment region 20 and the collar-shaped element 50. The bending region 40 has an end 41 facing toward the abutment region and an end 42 facing toward the anchoring region. The collar-shaped element 50 adjoins the bending region 40, on the end 42 thereof facing toward the anchoring region. The bearing region 60 in turn adjoins the collar-shaped element 50, and is therefore arranged between the collar-shaped element 50 and the anchoring region 30.

In the design of the implant 10 shown in FIG. 1, the abutment region 20 is designed as an abutment cone or conical part or element, which tapers toward the free or coronal end 22 of the abutment region 20. Conical elements enable a stable connection, of abutment region 20 and prosthetic construction (not shown) here.

The anchoring region 30 has a first threaded portion 33 and a second threaded portion 35, wherein the first threaded portion 33 is arranged between the bearing region 60 and the second threaded portion 35. The first threaded portion 33 is designed in this embodiment as a double-start thread having a lesser flank depth (in comparison to a flank depth of the second threaded portion) for the anchoring in the more solid, cortical component of the jaw bone, while the second threaded portion 35 is designed as a single-start thread having greater flank depth for the anchoring in the spongy region of the jaw bone. Both threaded portions have the same pitch here, so that no conflicts occur during the insertion of the screw profile.

Each of the threaded portions can have a cutting edge, the first threaded portion 33 has the cutting edge 34 and the second threaded portion 35 has the cutting edge 36. The cutting edges are arranged on the respective ends of the threaded portions facing away from the abutment region (apical ends). The threaded portions 33, 35 are thus provided as a self-tapping thread.

As already described above, the cutting edges 34, 36 on the thread flanks (and possible chip flutes) are designed so that the implant forms a thread structure itself with increasing screwing-in depth into the jaw bone. The screwing in is made easier by a preformed cavity. The bone thread thus resulting results by cutting or by displacement, whereby the screwing-in characteristic and the clamping properties, i.e., the primary stability, are determined.

In addition to the thread-shaped macrostructure, the region of the artificial tooth root is preferably provided with a roughened microstructure in particular, produced by application or targeted ablation. These rough structures are used, on the one hand, for exciting the bone accretion, on the other hand, for the permanent fixed interlocking with the bone after the healing phase. Such microstructures are created, for example, by blasting methods, by etching methods, or by a combination of these two ablation methods, or by an application method, for example, coating with a titanium plasma spray layer.

The thread (threaded portions) shown here is a so-called expansion thread, which clamps itself in the bone bed with increasing screwing-in depth, and which has a flank geometry varying over the thread length in addition to the conical thread base. In addition to threads having cylindrical outer shape and conical thread base, threads having conical outer geometry and cylindrical or conical thread base are possible. Alternatively to these thread shapes, other thread shapes are also conceivable, thus, for example, thread shapes which are well suitable for self-tapping threads.

The bending region 40 has a constricted geometry, having a smallest cross section 43, which is arranged in a half of the bending region 40 facing toward the anchoring region 30. The cross section of the bending region is designed as continuously enlarging in this embodiment, originating from the smallest cross section 43 toward the end 41 of the bending region facing toward the abutment region. The bending region 40 is designed as conical here (in each case conically widening, originating from the smallest cross section). A concave or convex enlargement or expansion of the cross section is also possible. The end 41 of the bending region which faces toward the abutment region 20 has a radius or a radius-shaped geometry 46, to avoid notches. The continuous enlargement is also continued over the radius-shaped geometry.

Because of the special design of the bending region 40, the bending region 40 experiences a targeted distributed plastic deformation, which is non-materially-damaging, in the event of corresponding bending stress.

The cross section of the bending region is also designed as continuously enlarging in this embodiment, originating from the smallest cross section 43 toward the end 42 of the bending region facing toward the anchoring region. A radius-shaped geometry, a second radius-shaped geometry 47, which causes the continuous enlargement of the cross section of the bending region, is also arranged between the smallest cross section 43 and the end 42 of the bending region 40 which faces toward the anchoring region 30. A soft transition is therefore ensured in the direction of the anchoring region and the bending region has a sufficiently high stability on its end 42 facing toward the anchoring region.

That is to say, to avoid notches, the end zone of the bending region is also designed here having a radius or the radius-shaped geometry 47, which causes the enlargement of the cross section, originating from the smallest cross section 43 toward the end of the bending region in the direction of the anchoring region. The smallest cross section 43 is therefore arranged on the radius-shaped geometry on the end 42 of the bending region 40 facing toward the anchoring region.

The collar-shaped element 50 adjoins the bending region 40. The bending region 40 is also used for the accumulation of the oral mucosa as a result of its design, in addition to the design as a bending zone. Due to the tapered geometry and the adjoining collar (collar-shaped element) 50, a barrier results against the penetration of microbes from the oral cavity into the region of the bony anchoring in the form of a labyrinth. In addition, the collar-shaped element 50 is used as a reinforcement. That is to say, in the region of the collar-shaped element 50 of the implant 10, the achieved deformation during bending of the bending region 40 is equal to zero because of the reinforcing effect.

Finally, the implant 10 has the bearing region 60. In this embodiment, the bearing region 60 is designed as a groove-shaped region or also as a groove-shaped element, for example, a channel, and is therefore provided depressed in relation to the surroundings. The bearing region 60 is provided for the purpose of receiving a device for bending the implant via this zone (bearing region). The groove-shaped region therefore forms a mounting region (bearing region) in which the device can engage.

In addition, for bending the implant, a further mounting region (torque-stable mounting region) is provided, on which the device for bending can engage, here, for example, on the free end 22 of the abutment region 20. In practice, it is expedient for the entire abutment region to be used as the mounting region. The implant may therefore be grasped or positioned in the device via the two mounting regions in a suitable manner and subsequently brought into the desired shape.

The implant extends in an extension direction or longitudinal direction 70. The respective cross section of the implant (essentially of the bending region here) extends transversely to the extension direction 70.

Figure 2B:
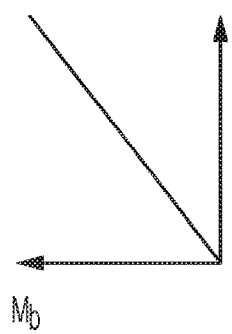
FIG. 2B shows a graph: curve of the bending torque.
Figure 2A:
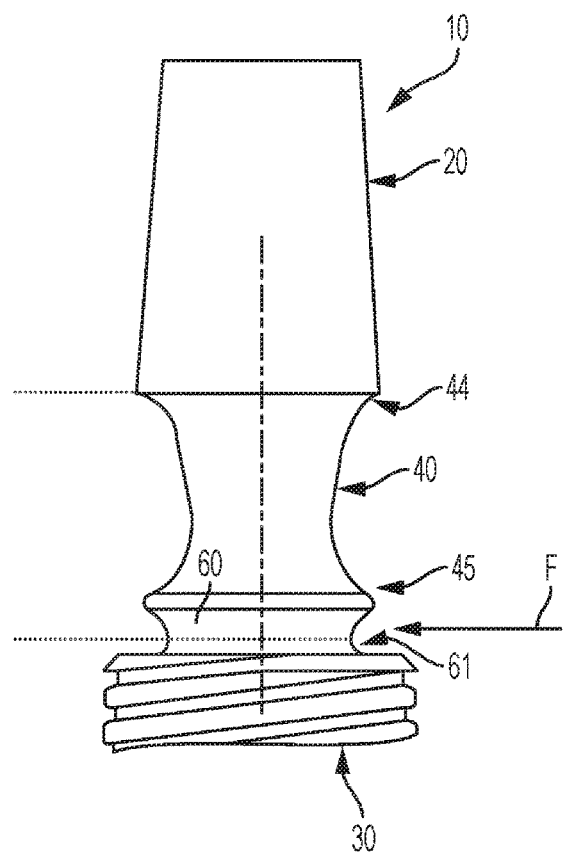
FIG. 2A shows a portion of the implant from FIG. 1.

FIG. 2A shows a portion of the implant from FIG. 1, in particular abutment region 20, bending region 40, collar-shaped element 50, and bearing region 60. More specific details in this regard are described with the following statements.

Figure 3:
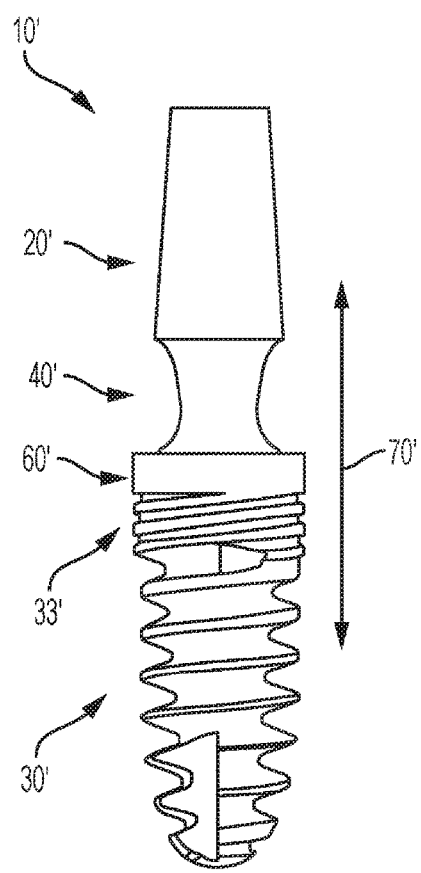
FIG. 3 shows a further embodiment of an implant according to the invention.
Figure 4:
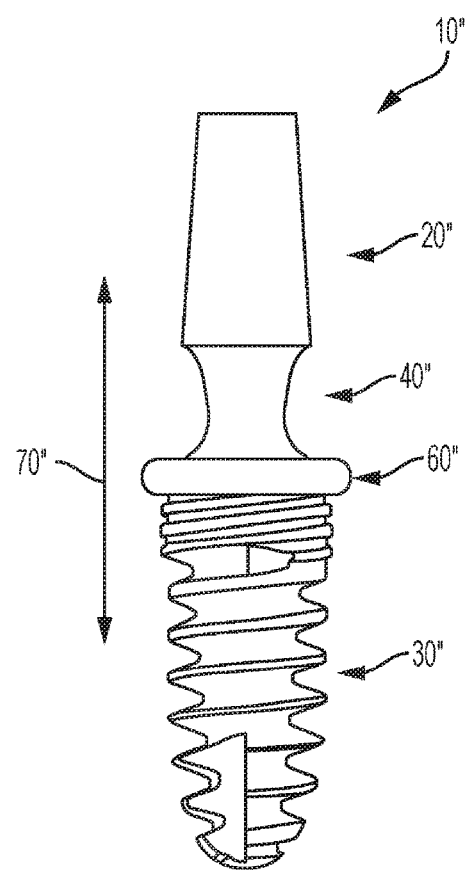
FIG. 4 shows a further embodiment of an implant according to the invention.

FIGS. 3 and 4 show alternative embodiments of the implant. FIG. 3 shows implant 10' having abutment region 20', anchoring region 30', and bending region 40'. The remaining components of the implant correspond to those from FIG. 1 and are therefore not explicitly described once again. A bearing region 60' is designed here as an enlarged region in relation to the bending region 40', which corresponds, for example, in this embodiment to the shape and the diameter of a first threaded portion 33' of the anchoring region 30' and is designed as disk-shaped, for example. The edge region of the bearing region 60' is designed as linear here in the extension direction 70' of the implant 10'. Larger or smaller designs, both in the extension direction 70' and also transversely thereto, would also be possible. It is to be focussed on the implantation region in the jaw.

FIG. 4 shows an implant 10" having abutment region 20", anchoring region 30", and bending region 40". The remaining components of the implant correspond to those from FIG. 1 and are therefore not explicitly described once again. A bearing region 60" is also designed as disk-shaped here, however, the edge region is designed as rounded, i.e., it bulges outward. In this embodiment, the bearing region 60" protrudes beyond the anchoring region 30" transversely to an extension direction 70" of the implant 10".

In both cases, no explicit collar-shaped element is provided as a result of the design of the bearing regions. In particular due to the design of the bearing region 60" according to FIG. 4, an obstruction is nonetheless provided (but also by the bearing region 60'), which can prevent the penetration of microbes into the jaw region. Both the bearing region 60' and also the bearing region 60" can also be viewed as a type of collar-shaped element.

As can be inferred from FIG. 1, a smallest cross section of the bearing region 60 is designed as larger than the smallest cross section 43 of the bending region 40. This promotes the defined bending operation. The smallest cross sections of the bearing regions 60', 60" are also designed to be larger than the smallest cross section of the bending region in the case of the implants 10' and 10" according to FIGS. 3 and 4.

Figure 5A:
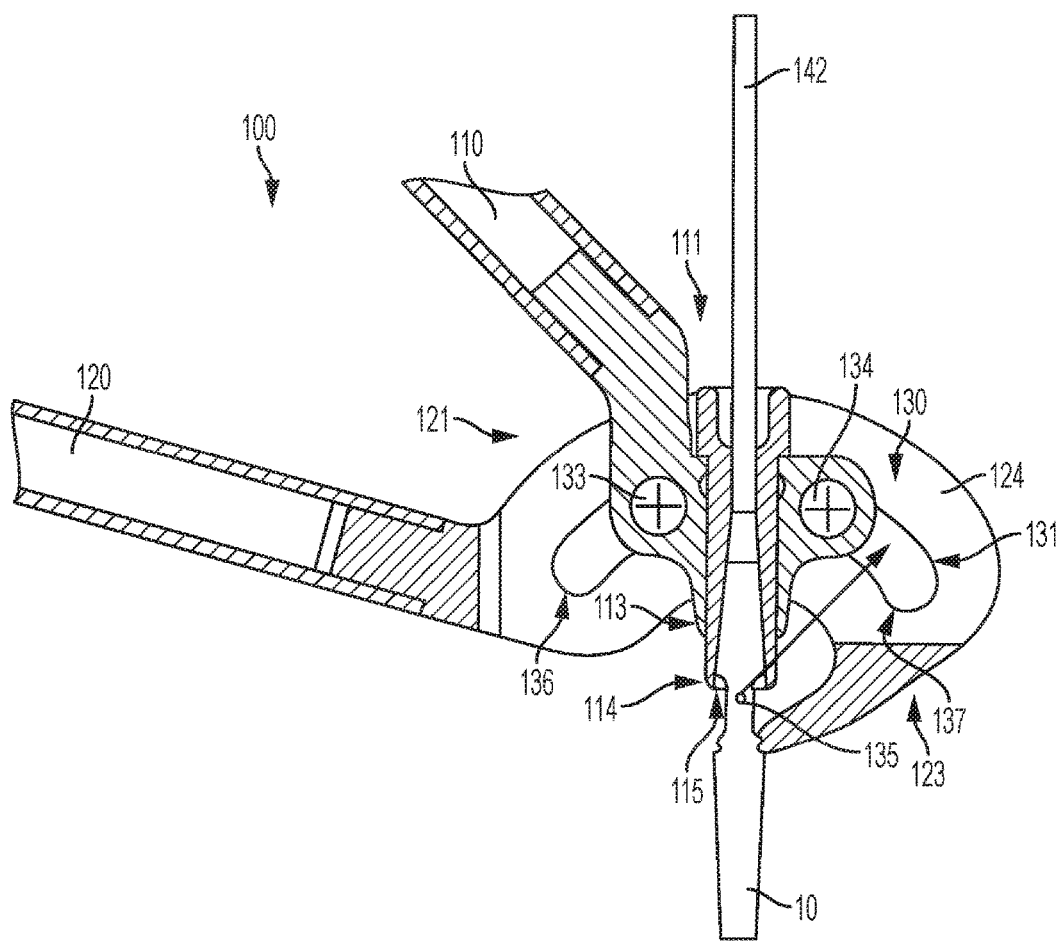
FIG. 5A shows an embodiment of a device according to the invention for bending an implant in a sectional illustration.
Figure 5B:
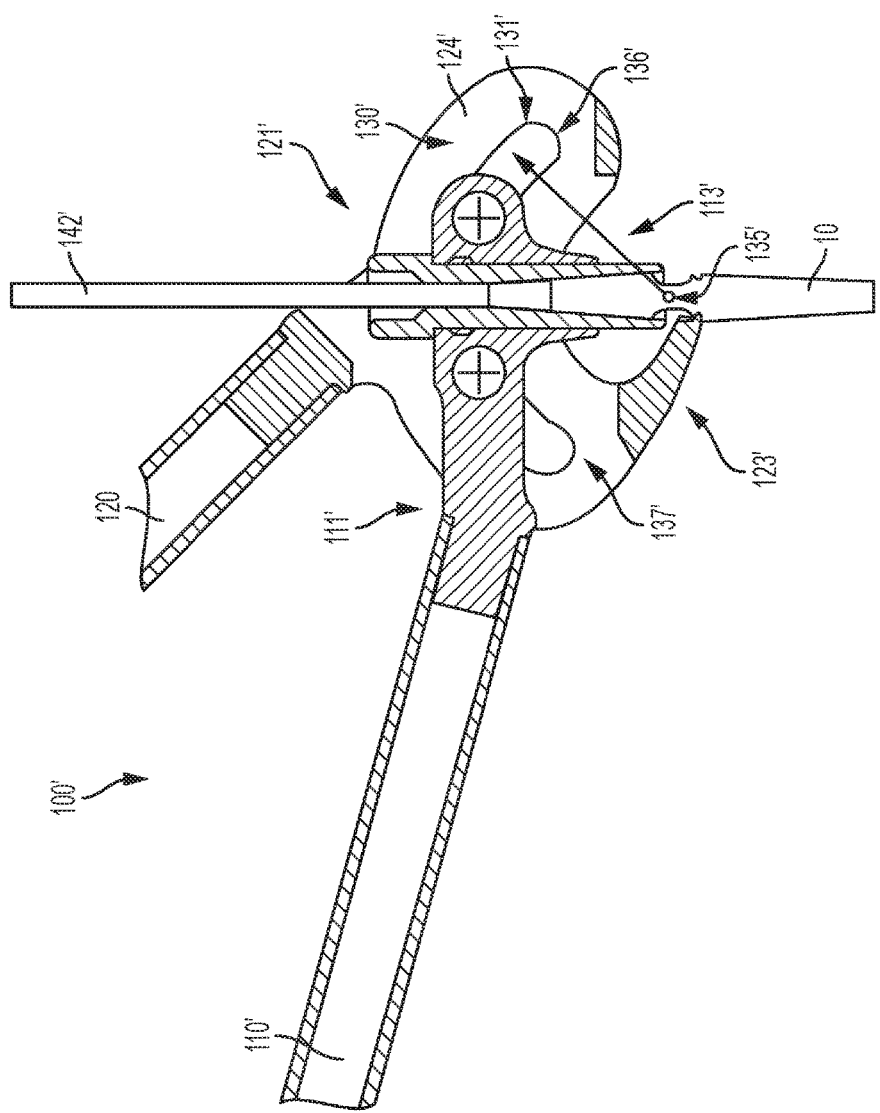
FIG. 5B shows a further embodiment of a device according to the invention for bending an implant in a sectional illustration.

FIG. 5A shows an embodiment of a device 100 according to the invention for bending an implant, FIG. 5B shows a further embodiment 100' of a device according to the invention for bending an implant. The embodiment according to FIG. 5A shows a device for bending an implant as described above, for example, wherein the device is designed such that the bending of the implant, i.e., of the abutment region in relation to the anchoring region via the bending region, takes place in the direction of the oral opening (toward the operator). The arrangement according to FIG. 5B enables bending in the direction of the oral cavity (away from the operator).

Figure 6A:
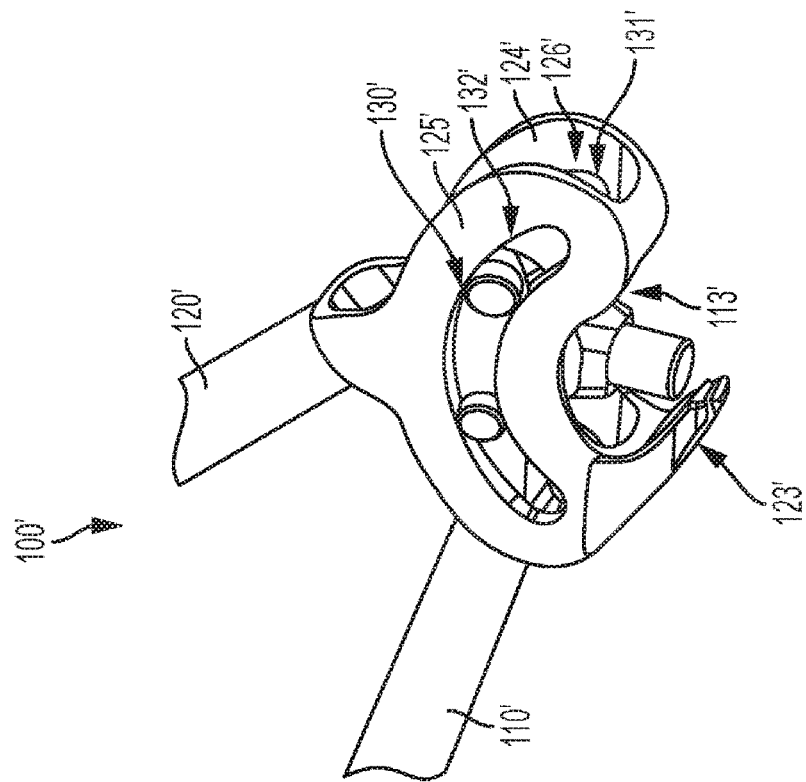
FIG. 6A shows the embodiment according to FIG. 5A in a perspective view.
Figure 6B:
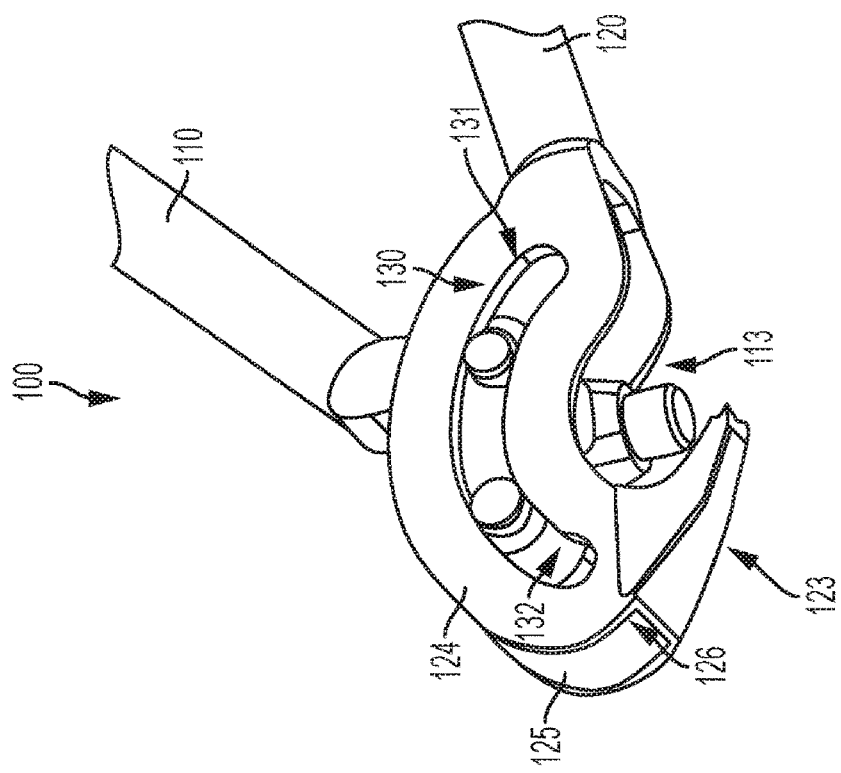
FIG. 6B shows the embodiment according to FIG. 5B in a perspective view.
Figure 7B:
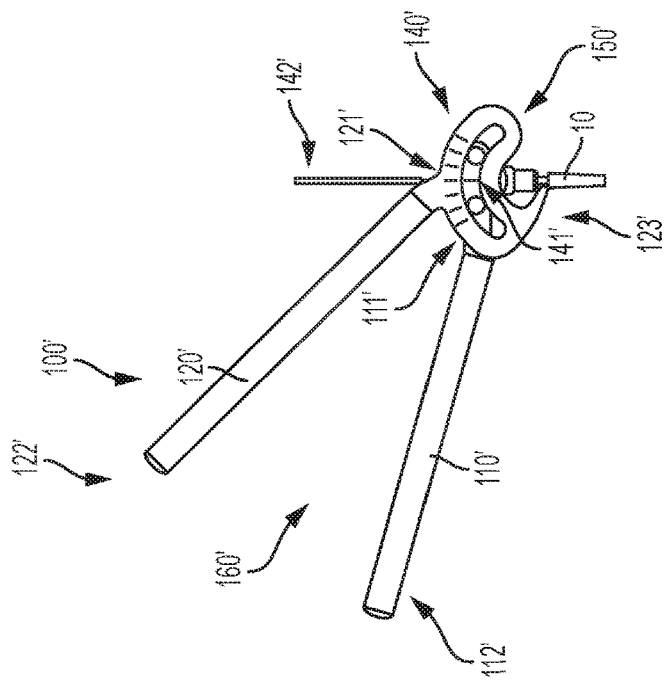
FIG. 7B shows the embodiment according to FIG. 5B in a side view.
Figure 7A:
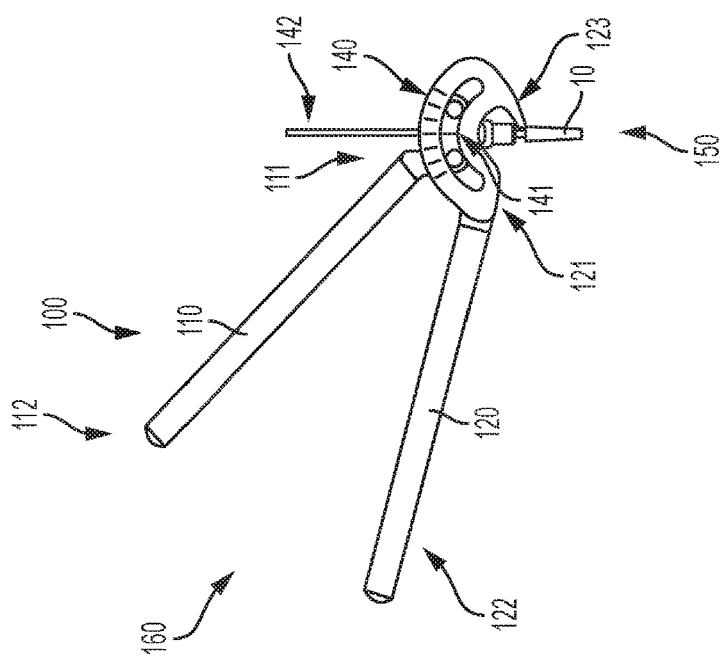
FIG. 7A shows the embodiment according to FIG. 5A in a side view.

A differentiation is made hereafter between the embodiments according to FIGS. 5A, 6A, and 7A, on the one hand, and according to FIGS. 5B, 6B, and 7B, on the other hand, so that for the device for bending in the direction of the oral opening (FIGS. 5A, 6A, and 7A), the reference sign 100 is used, while for the device for bending in the direction of the oral cavity (FIGS. 5B, 6B, and 7B), the reference sign 100' is used. This applies accordingly to the individual components, although they are not completely specified under certain circumstances in FIGS. 5B, 6B, and 7B (since they are already illustrated in FIGS. 5A, 6A, and 7A).

FIGS. 6A and 6B show the embodiments according to FIGS. 5A and 5B in a perspective view.

The device for bending the implant, which is also referred to as a bending device, bending instrument, or bending pliers, will be described in detail hereafter on the basis of FIGS. 5A and 6A. As can be inferred from FIG. 5A, the device has a first branch or a first leg 110 and a second branch or a second leg 120. A holding unit 113 is provided on a distal end 111 of the first leg 110 for receiving the abutment region 20, for example, of the implant 10, 10', 10", as described above with FIGS. 1 to 4. Implant 10 is shown here as an example. The holding unit has a sleeve 114 in this embodiment, in which the implant 10 is receivable via an opening 115 of the sleeve (sleeve opening). The opening is arranged and designed such that it can face toward the implant, in particular also when the implant is already anchored in the jaw bone.

The sleeve 114 is, for example, fixedly connected via a mechanical connection to the first leg 110. The abutment region 20 of the implant 10 is received in a bending-torque-stable manner in the holding unit 113, i.e., in the sleeve 114. The implant 10 is positioned in the device by being received in the sleeve 114. The holding unit 113 or at least the sleeve-shaped part is replaceable for different abutment geometries, i.e., geometries of the abutment region.

A support unit 123, which is held via plate elements 124 and 125 (see FIG. 6A), is provided on a distal end 121 of the second leg 120. Only plate element 124 is visible in FIG. 5A. FIG. 6A shows the first plate element 124 and the second plate element 125, which are spaced apart opposite to one another and form a cavity 126 in between. The holding unit 113 extends in this cavity on the distal end 111 of the first leg 110. The support unit 123 is designed in this embodiment as a hooked element connecting the plate elements.

The plate elements 124, 125 are part of a guide unit 130, which articulately joins the legs 110, 120 with one another, so that the legs and therefore the holding unit and the support unit are movable in relation to one another on a defined path, preferably in an arc shape. The guide unit 130 is thus designed such that the legs and therefore the holding unit and the support unit are movable in relation to one another in a defined manner.

Both the first plate element 124 and also the second plate element 125 each have a guide path 131, 132 (first guide path 131, second guide path 132). Pin elements are inserted therein as guide elements 133, 134 of the guide unit 130 (a guided connection may also be implemented via other elements). The pin elements 133, 134 are arranged or fastened in this embodiment on the distal end 111 of the first leg 110 and establish a connection between the legs 110 and 120 by engaging in the guide paths. The guide unit is designed here as a slotted guide and enables the pivoting of the legs, i.e., the relative movement of the branches or legs toward one another.

The guide paths are designed here as slots and therefore as openings. The guide paths could also be designed as grooves.

As can be inferred from the figures, the two pin elements 133, 134 (guide elements) are arranged on the distal end 111 of the first leg 110 such that the holding unit is arranged between the pin elements. Each of the pins engages with one end in the first guide slot 131 on the first plate element 124 and with the other end in the second guide slot 132 on the second plate element 125.

Because of the slotted guide, the movement possibility is predefined, i.e., only a defined movement of the legs is possible. The slotted guide is thus designed so that the relative movement of the two pliers legs and therefore of the holding unit and the support unit is performed on a defined path. That is to say, a reference to the bending line of the bending region is produced, the movement follows or essentially follows the bending line of the bending region or defines the bending line of the bending region. A bending angle is therefore also predefined, i.e., the maximum angle which is achievable between the abutment region and the anchoring region of the implant by means of the device 100.

The first pliers leg 110 is thus guided in relation to the second pliers leg 120 in the slotted guide. According to the mechanical chucking conditions, the center point 135 of the slotted guide, which is designed as circular here, lies close to or in the plane of the fixed chucking, i.e., in the boundary plane between abutment region (abutment cone) and bending region (bending zone). Alternatively to the circular slotted guides, depending on the requirements for the bending line, other geometries/curve shapes, for example, ellipses, can be provided.

The relative movement of the legs in relation to one another and therefore a closing movement of the legs enables the bending of the implant, so that a defined bending angle can be generated between abutment region and anchoring region of the implant.

The guide paths 131, 132 each have delimitations 136, which delimit the maximum settable bending angle. This maximum bending angle is dimensioned so that no damage to the material microstructure and therefore no reduction of the mechanical properties of the implant can occur during bending of the tooth implant.

The guide unit 130 is designed such that the guide elements 133, 134 can be guided without play.

In order that, for the intraoral bending procedure, the implant already implanted in the jaw bone can be simply positioned in the sleeve 114 of the bending device 100, the guide paths 131, 132 each have a widening region 137. The guide element, which faces toward the widening region, can be introduced into this widening region with maximum opening of the pliers legs in the end position, so that the pliers legs may be opened still further. This enables simpler positioning of the device on the abutment region protruding out of the jaw bone, abutment cone 20 here, of the implant. Due to the closing movement, the guide element slides back into the actual guide paths.

The holding unit 113 has a further opening, which is opposite to the opening 115. A pointer unit 142 is arranged in this opening, which enables the monitoring of the bending procedure. Via the pointer unit 142, the orientation of the bent implant, i.e., of the abutment region, in relation to the row of teeth of a patient is displayable (in relation to the adjacent implants or to the natural dentition). That is to say, the present bending angle can be judged by means of the pointer unit 142, which indicates the present alignment of the abutment region 20.

The relative position of the branches or pliers legs 110, 120 and therefore the present bending angle can be read off on a scale 140 (see FIG. 7A). For this purpose, a corresponding marking 141 is provided on the distal end 111 or on the holding unit 113. The over-bending angle required for lasting deformation can also be read off by means of the scale.

FIGS. 5B and 6B show, as already mentioned above, a further embodiment of a device 100' according to the invention for bending an implant. In principle, this embodiment has the same elements as already described with the embodiment according to FIGS. 5A and 6A, except the device is designed such that the implant 10, in particular the abutment region, is bendable in the direction of the oral cavity (in contrast to the direction of the oral opening). The monitored bending procedure is thus carried out by a closing movement of the pliers legs either in the direction of the oral opening (embodiment of the device according to FIGS. 5A, 6A, 7A) or in the direction of the oral cavity (embodiment of the bending pliers according to FIGS. 5B, 6B, 7B), since it is necessary for the use of the bending device on the patient that implants can be bent both in the direction of the oral opening and also in the opposite direction, i.e., in the direction of the oral cavity.

In the embodiment according to FIGS. 5B, 6B (see also FIG. 7B), the support unit 123' is thus arranged such that it faces in the direction of the distal end 150' of the device 100', in the embodiment according to FIGS. 5A, 6A (see also FIG. 7A), the support unit 123 is arranged such that it faces in the direction of the proximal end 160 of the device 100. The embodiment in which the support unit 123' faces in the direction of the distal end 150' of the device enables bending of the implant in the direction of the oral cavity, while the embodiment in which the support unit 123 faces in the direction of the proximal end 160 of the device enables bending of the implant in the direction of the oral opening. The monitored bending procedure is thus carried out either in the direction of the oral opening or in the direction of the oral cavity by a closing movement of the pliers legs. However, the support unit is always arranged on the distal end of the second leg.

The support unit is in particular designed and/or arranged such that it is applicable to the bearing region of the implant during a closing movement of the legs and/or the force can be introduced into the bearing region of the implant during a closing movement of the legs.

Alternatively to the use of two devices for bending an implant for both bending directions, a pliers having two support units can also be provided, wherein these support units then have to be able to be advanced and/or adjusted. The support units are then to be, for example, replaceable or separately positionable.

It is to be noted in this case that the support unit which is not in action (i.e., the support unit which is not required), can be placed on the device such that it does not interfere during the treatment in the jaw region of a patient. As already stated above, the support unit is designed such that only a small region of the gum and of the bone tissue in the surroundings of the implant bearing is to be surgically exposed to carry out the bending procedure on the alveolar ridge. A possible second unit therefore has to be placed on the device so that it does not impair the working region and above all does not damage the implantation region, i.e., the tissue.

FIGS. 7A and 7B show the embodiments according to FIGS. 5A and 5B in a side view. In this case, the bending devices 100, 100' are each shown completely. The proximal ends of the legs are now visible, the proximal end 112, 112' of the first leg 110, 110' and the proximal end 122, 122' of the second leg 120, 120'. The pointer unit 142, 142' is also arranged on each of the bending devices 100, 100'. The scale 140, 140' is provided in each case on one of the plate elements, but can also be arranged on each of the plate elements. The marking 141, 141' is applied or arranged, for example, between the respective pin elements.

The distal end 150 and the proximal end 160 of the device 100 and the distal end 150' and the proximal end 160' of the device 100' are also shown.

Moreover, FIGS. 5B, 6B, 7B also show the distal ends 111', 121' of the first leg 110' or of the second leg 120', respectively, the holding unit 113', the support unit 123', the guide unit 130' having the first plate element 124', the second plate element 125', and the cavity 126' provided between the plate elements. The plate elements have the guide paths 131' and 132'. In FIG. 5B, the center point 135' of the slotted guide, which is designed as circular here, is indicated, as well as the delimitation 136' and the widening 137' of the visible guide path. Sleeve, opening, and pin elements are not explicitly identified, but correspond to those from FIGS. 5A, 6A, and 7A.

FIG. 8 shows a detail from the implant 10 (from FIG. 1) having bending region 40, collar-shaped element 50, bearing region 60, and partially anchoring region 30. The support unit 123 (or 123') engages in a formfitting manner in the bearing region 60 of the implant or thereon and is used as a counter bearing (bearing) during the bending procedure.

FIG. 9 shows a portion of the support unit 123 and a cross-section of a portion of the implant 10 taken along a line 9-9' of FIG. 8, in a view from below, as the support unit 123 engages in the groove-shaped bearing region 60 of the implant 10 or approaches it. The support unit is designed as arc-shaped in this embodiment at one end, the engagement end 123a, which is provided for engaging on the bearing region, and can thus cling to the bearing region. The bulge of the end extends in the direction of the support unit. The implant 10 is shown in section here, wherein the section is provided transversely to the extension direction 70 of the implant, in the bearing region 60.

If implants are to be bent using the bending device, as are shown, for example, in FIGS. 3 and 4, bending would thus also be executable using the support unit 123 or 123'. In both cases, clinging of the support unit 123 via the engagement end 123a on the bearing region 60' or 60'' is also possible.

In the case of, for example, polygonal or square bearing region (flattened sides), lateral tips of the engagement end can come to rest on the bearing region, i.e., can engage thereon. The engagement end 123a could also have a different shaping.

The device 100, 100' for bending the implant, i.e., the bending device, is actuatable and usable as follows:

The abutment region 20 of the tooth implant 10 is inserted into the holding unit 113, 113', i.e., into the sleeve 114 here, and thus held in a formfitting manner in the holding unit 113, 113'. Because of the form fit of sleeve and abutment region of the implant, the device thus centers itself on the implant. The form fit does not preclude a ring gap from being provided between chucked implant 10 and sleeve 114, to avoid jamming of the abutment region 20 in the holding unit 113, 113'. The holding in the holding unit is combinable with the mounting of the implant via the only locally touching support unit, which can be placed or positioned on the bearing region 60, more precisely on a portion 61 of the bearing region 60 of the implant 10 (or also another object) without jamming. The implant 10 is therefore positionable in the bending device 100, 100' and thus prepared for the subsequent bending procedure. Alternatively to the bearing region 60 shown here, of the groove-shaped region, other locations on the implant can be used for the force introduction.

The legs 110, 110' and 120, 120' can be actuated correspondingly to a pliers, scissors, or clamping tool, wherein the guide elements, the pin elements 133, 134 here, can be guided without play in the guide slots 131, 131', 132, 132'. The bending angle is predefined by the design of the guide slots 131, 131', 132, 132'. Handling of the legs is possible via the proximal ends 112, 112' or 122, 122' thereof. These ends are graspable by the operator and can have corresponding handle elements.

A bending force F (see, for example, FIG. 2A) is introduced by the closing of the legs into the geometry of the bearing region 60, in particular in a portion 61 of the bearing region 60, by means of the support unit 123, 123' (which is arranged accordingly). The geometry of the bending region is designed between the bearing region 60 and the formfitting or bending-torque-stable holding of the abutment region 20 so that in the event of bending stress, a controlled deformation takes place in the material volume of the bending region 40.

As can be inferred from the graph in FIG. 2B, an increasing bending torque Mb (increasing over the length 1 of the bending region) is generated, originating from the engagement location of the support unit in the bearing region of the implant (force F) toward to the chucking at the abutment region. Since the device for bending (bending instrument) neutralizes the forces and torques between bearing region and abutment region, the enossal region and therefore the bone surrounding the anchoring region do not experience forces or torques from the bending process.

The implantation is performed so that the end of the first threaded portion 33 facing toward the abutment region 20 lies at or slightly below the bone level 80. As a result of the anatomical conditions, i.e., the curvature of the alveolar ridge, the bearing region 60 then lies either above the bone level or partially also at or slightly below the bone level.

Figure 10:
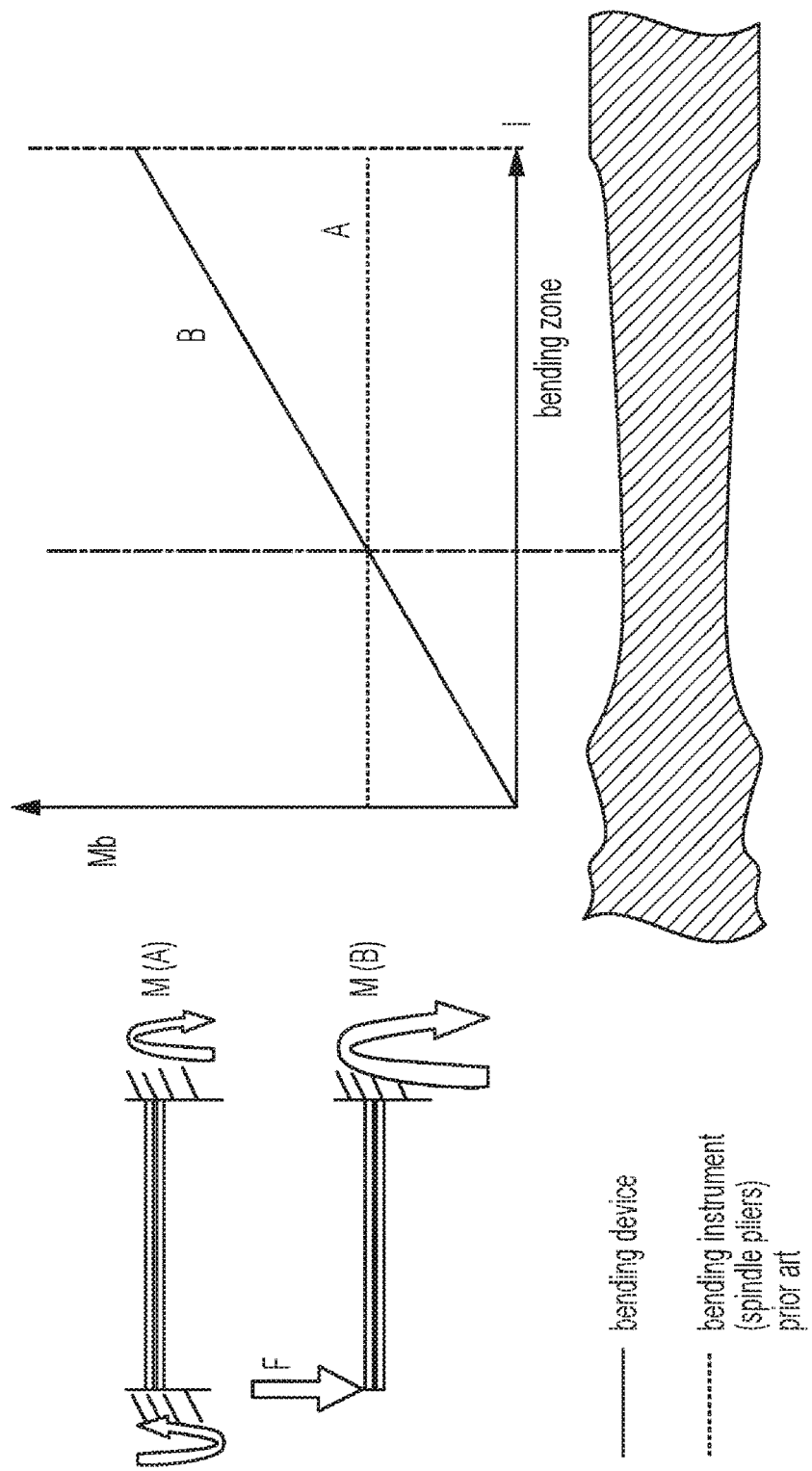
FIG. 10 shows a comparison: prior art—device according to the invention for bending an implant.

FIG. 10 shows a comparison in the use of a bending device from the prior art (EP 2 438 885 A1, spindle pliers, see under A) and the use of the bending device according to the invention (see under B). The known device requires fixed chucking on both sides of the bending region of the implant, once in a formfitting manner on the bending collar (collar-shaped region) and once in a formfitting manner on the abutment cone, so that a bending torque is introduced on both sides. Due to this chucking and load introduction, a stress in the form of a constant bending torque Mb is generated over the length 1 of the bending region in the bending region. In contrast to the torque-stable chucking on both sides, the bending method according to the invention using one-sided chucking generates an increasing bending torque Mb, originating from the engagement location of the support unit in the bearing region of the implant toward the chucking in the abutment region (see also FIG. 2B).

Fundamentally, using the device for bending, any other object may also be bent, which is positionable in the device. In this case, bending is also possible in the anchor-free state. However, the goal in particular is to deform an already implanted, i.e., anchored tooth implant so that damage to the bone bed is avoided, wherein the region on the alveolar ridge is to be treated as carefully as possible.

Studies on the Bending Region According to the Invention of the Implant

The implant according to the invention has the special design of the bending region. If a bending region having constant cross section or a cross section tapering from apical to cervical is used in the one-sided chucking, it would thus bend in a buckled manner close to the chucking at the abutment region. This arrangement would already result in damage to the microstructure at small bending angles, because of the stress concentration close to the chucking at the abutment region. That is to say, greater bending angles without microstructure damage could not thus be generated.

A method for judging the deformability of a material, in the present case bending multiple times, is numeric analysis using the method of finite elements. In addition to the consideration of the elastoplastic behavior, experimentally ascertained fracture limit curves (achievable plastic elongation as a function of the stress state) are specified for these simulations. A failure can take place in this case due to ductile normal fracture (DNF) or due to ductile shear fracture (DSF). The occurrence of fracture is assessed by the corresponding fracture risks (fracture risk>1.0 means failure). The difference of the ascertained value DNF or DSF to 1.0 is a measure of the security or the reserve until the occurrence of a fracture in the material.

If a geometry, as is provided in a bending region according to FIG. 2A, 3, or 4, is studied with respect to the possible damage of the material in the case of maximum practically-relevant bending (worst-case stress) of the implant of 20°, followed by bending back by 10°, followed by a further bending of 5°, it has been shown that for a suitable (see above) material to be used here (the proposed material group), the damage-describing values DNF=0.42 and DSF=0.29 result. Therefore, in each case a safety factor 2 is provided against fracture in the case of the worst case stress.

LIST OF REFERENCE NUMERALS

- 10, 10', 10" implant
- 20, 20', 20" abutment region
- 21 end facing toward the anchoring region
- 22 free end, coronal end
- 30, 30', 30" anchoring region
- 31 end facing toward the abutment region
- 32 free end, enossal end
- 33, 33' first threaded portion
- 34 cutting edge of first threaded portion
- 35 second threaded portion
- 36 cutting edge of second threaded portion
- 40, 40', 40" bending region
- 41 end facing toward the abutment region
- 42 end facing toward the anchoring region
- 43 smallest cross section
- 44 cross section on the end facing toward the abutment region, cervical cross section
- 45 cross section on the end facing toward the anchoring region, apical cross section
- 46 first radius-shaped geometry
- 47 second radius-shaped geometry
- 50 collar-shaped element
- 60, 60', 60" bearing region
- 61 portion of bearing region
- 70, 70', 70" extension direction, longitudinal direction of implant
- 80 bone level
- 100, 100' device for bending (instrument)
- 110, 110' first leg, first branch
- 111, 111' distal end of first leg
- 112, 112' proximal end of first leg
- 113, 113' holding unit
- 114 sleeve
- 115 opening
- 120, 120' second leg, second branch
- 121, 121' distal end of second leg
- 122, 122' proximal end of second leg
- 123, 123' support unit
- 123a engagement end
- 124, 124' first plate element
- 125, 125' second plate element
- 126, 126' cavity
- 130, 130' guide unit
- 131, 131' first guide path
- 132, 132' second guide path
- 133 guide element, pin element
- 134 guide element, pin element
- 135, 135' center point
- 136, 136' delimitation
- 137, 137' widening region
- 140, 140' scale
- 141, 141' marking
- 142, 142' pointer unit
- 150, 150' distal end of device
- 160, 160' proximal end of device
- Mb bending torque
- F force
- l length of bending region

The invention claimed is:

1. A device for bending an implant anchored in a maxilla or a mandible, comprising:
    a first leg and a second leg articulately jointed with each other and actuatable corresponding to a scissors tool,
    a holding unit disposed at a distal end of the first leg for fixing of at least a portion of an abutment region of the implant, wherein the holding unit has a sleeve arranged such that the implant, when anchored in the maxilla or the mandible, is receivable in the sleeve via an opening of the sleeve, such that the implant is held in the holding unit in a formfitting manner, and
    a support unit disposed at a distal end of the second leg for introducing a force into a bearing region of the implant, wherein the support unit is designed such that a portion of the bearing region of the implant is graspable without jamming.

2. The device as claimed in claim 1, characterized in that the holding unit and the support unit are movable in an arc shape in relation to one another by means of the first leg and the second leg.

3. The device as claimed in claim 1, characterized in that the holding unit is capable of fixing the at least a portion of the abutment region of the implant in a bending-torque-stable manner.

4. The device as claimed in claim 1, characterized in that the sleeve is replaceable.

5. The device as claimed in claim 1, characterized in that the support unit is designed either:
    as a one-part element;
    (ii) as a hooked element;
    (iii) such that the force can be introduced into the bearing region on one side,
    (iv) such that the force can be introduced into the bearing region in the bending direction; or
    (v) such that it can be applied to a single portion of the bearing region.

6. The device as claimed in claim 1, characterized in that a pointer unit is arranged on the holding unit, such that an orientation of the implant in relation to a row of teeth of a patient is displayable.

7. A device for bending an implant anchored in a maxilla or a mandible, comprising:
- a first leg and a second leg articulately jointed with each other and actuatable corresponding to a scissors tool,
- a holding unit disposed at a distal end of the first leg for fixing of at least a portion of an abutment region of the implant,
- a support unit disposed at a distal end of the second leg for introducing a force into a bearing region of the implant, and
- a guide unit comprising at least one slotted guide path for articulately joining the legs with one another and for moving the legs in relation to one another, wherein the slotted guide path defines a bending line of the implant.

8. The device as claimed in claim 7, characterized in that the at least one slotted guide path of the guide unit is arranged on the distal end of the second leg, and the guide unit further comprises at least one guide element, which is arranged on the distal end of the first leg, wherein the guide element can be guided in the slotted guide path.

9. The device as claimed in claim 7, characterized in that a scale is arranged along the slotted guide path, and a marking is arranged on the distal end of the first leg such that a bending angle of the implant between the abutment region and an anchoring region is displayable.

10. The device as claimed in claim 7, characterized in that the slotted guide path has an enlarged region at an end of the slotted guide path such that a guide element facing toward the enlarged region is receivable therein upon maximum opening of the legs.

11. A device for bending an implant anchored in a maxilla or a mandible, comprising:
- a first leg and a second leg articulately jointed with each other and actuatable corresponding to a scissors tool,
- a holding unit disposed at a distal end of the first leg for fixing of at least a portion of an abutment region of the implant, wherein the holding unit has a sleeve arranged such that the implant, when anchored in the maxilla or the mandible, is receivable in the sleeve via an opening of the sleeve, such that the implant is held in the holding unit in a formfitting manner, and
- a support unit disposed at a distal end of the second leg for introducing a force into a bearing region of the implant, wherein the support unit is designed such that the bearing region of the implant is graspable only on a portion which is arranged on a side of the implant which is to be elongated.

12. The device as claimed in claim 11, characterized in that the holding unit and the support unit are movable in an arc shape in relation to one another by means of the first leg and the second leg.

13. The device as claimed in claim 11, characterized in that the holding unit is capable of fixing the at least a portion of the abutment region of the implant in a bending-torque-stable manner.

14. The device as claimed in claim 11, characterized in that the sleeve is replaceable.

15. The device as claimed in claim 11, characterized in that the support unit is a one-part element.

16. The device as claimed in claim 11, characterized in that the support unit is a hooked element.

17. The device as claimed in claim 11, characterized in that the support unit is designed such that the force can be introduced into the bearing region on one side.

18. The device as claimed in claim 11, characterized in that the support unit is designed such that the force can be introduced into the bearing region in the bending direction.

19. The device as claimed in claim 11, characterized in that the support unit is designed such that it can be applied to a single portion of the bearing region.

\* \* \* \* \*